(12) United States Patent
Crooks et al.

(10) Patent No.: US 6,403,602 B1
(45) Date of Patent: *Jun. 11, 2002

(54) MORPHINE-6-SULFATE ANALOGUES AND THEIR USE FOR THE TREATMENT OF PAIN

(75) Inventors: Peter A. Crooks; Abdulghani A. Houdi, both of Lexington, KY (US); Santosh G. Kottayil, Schaumburg, IL (US); D. Allen Butterfield, Lexington, KY (US)

(73) Assignee: The University of Kentucky Research Foundation, Lexington, KY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/040,240

(22) Filed: Dec. 31, 1997

Related U.S. Application Data

(63) Continuation of application No. 08/881,288, filed on Jun. 24, 1997, now abandoned, which is a continuation-in-part of application No. 08/803,312, filed on Feb. 20, 1997, now abandoned.

(51) Int. Cl.$^7$ .......................... A61K 31/44; A61P 25/04; C07D 489/00
(52) U.S. Cl. ................................ 514/282; 546/44
(58) Field of Search ............................ 546/44; 514/282

(56) References Cited

U.S. PATENT DOCUMENTS

| | | | |
|---|---|---|---|
| 4,362,870 A | 12/1982 | Portoghese | 546/44 |
| 4,496,570 A | 1/1985 | Bodor | 546/15 |
| 5,219,861 A | 6/1993 | Kanematsu et al. | 546/44 |
| 5,258,512 A | 11/1993 | Heiman et al. | 546/44 |
| 5,629,011 A * | 5/1997 | Illum | 424/434 |
| 5,739,145 A * | 4/1998 | Nagase | 514/282 |

OTHER PUBLICATIONS

Beilstein, abstract registry No. 73 97 281, 1995.*
Sankyo, Chem. Abstr. vol. 96 Entry 218088, 1982.*
Brock et al., Chem. Abstr. vol. 124 Entry 161029, 1996.*
Aceto et al. Chem. Abstr vol. 125 entry 104826, 1995.*
Jacobson Chem. Abstr vol. 125 Entry 185591, 1996.*
Woods et al. Chem. Abstr. vol. 125 Entry 185592, 1996.*
Aceto et al Chem Abstr vol. 125 Entry 185593, 1996.*
Houdi et al., "3–O–Acetylmorphine–60–Sulfate: A Potent, Centrally Acting Morphine Derivative", Pharmacology Biochemistry and Behavior, vol. 53, No. 3, pp. 665–671, Mar. 1996.
Choonara et al., "Morphine Sulphation in Children", citied in Journal of Clinical Pharmacology, Dec. 1990, pp. 897–900. (see Abstract).
Hirano et al., "Synthesis and Pharmacological Activity of Sulfate Conjugate at 6–Position of N–Substituted Normorphine Derivatives, cited in Chemical Pharmaceutical Bulletin", Aug. 1991, vol. 39, No. 8, pp. 2000–4. (see Abstract).
Brown et al., "Analgesic Potencies of Morphine 3– and 6–Sulfates After Intracerabroventricular Administration in Mice: Relationship to Structural Characteristics Defined by Mass Spectrometry and Nuclear Magnetic Reseonance", Journal of Pharmaceutical Science, vol. 74, No. 8, pp. 821–824, Aug. 1985.
Oguri et al., "Potentiation of Physical Dependence by Conjugation at the 6–Position of Nalorphine", cited in European Journal of Pharmacology, Jul. 1984, vol. 102 No. 2, pp. 229–35. (see Abstract).

* cited by examiner

Primary Examiner—Brenda Coleman
(74) Attorney, Agent, or Firm—McDermott, Will & Emery

(57) ABSTRACT

3-O-Acetylmorphine-6-sulfate analogues are potent, centrally-acting morphine derivatives. The compounds are useful for the treatment of pain.

10 Claims, 16 Drawing Sheets

MORPHINE-6-SULFATE ANALOGUES AND THEIR USE FOR THE TREATMENT OF PAIN

RELATED APPLICATIONS

This application is a continuation of application Ser. No. 08/881,288 filed Jun. 24, 1997 now abandoned: which is a continuation-in-part of application Ser. No. 08/803,312, filed Feb. 20, 1997 now abandoned.

Technical Field

The present invention relates to 3-O-Acetylmorphine-6-sulfate compounds and their ester derivatives which are potent, centrally-acting morphine derivatives. The compounds are useful for the treatment of pain.

BACKGROUND ART

The opiate analgesic morphine, when administered to humans, is converted by the liver into three major metabolites, viz. morphine-3-O-glucuronide (M3G), morphine-6-O-glucuronide (M6G) and morphine-3-O-sulfate (M3S) [9,19]. M6G is found in the systemic circulation in concentrations exceeding those of morphine itself, after both parenteral [12,19] and oral administration [12,18]. M6G is a very potent μ-receptor agonist [3] with a high affinity for both $mu_1$ and $mu_2$ receptors [1,14] and appears to cross the blood-brain barrier in spite of its high polarity compared to morphine [20].

Some morphine compounds are known in the art. For example, U.S. Pat. No. 5,219,861 to Kanematsu et al. relates to a novel morphine-6-thiol derivatives. Kanematsu discloses acetylthio-derivatives on the six position of morphine and esters on position three.

U.S. Pat. Nos. 4,496,570 to Bodor and 5,352,680 to Portoghese et al. relates to opiates with heterocyclic substituents bound to position six of the opiate ring. Both patents disclose thiol ring substituents on morphine.

U.S. Pat. No. 4,362,870 to Portoghese relates to a non-addictive analgesic opiate. Portoghese further discloses morphine-like opiates which have substituted isothiocyanate groups on position six and ester groups on position three of the opiate.

U.S. Pat. No. 5,258,512 to Heiman et al. relates to a method for a fluorescence polarization immunoassay procedure for determining the amount opiate alkaloids in fluids. The invention discloses, in FIG. 13-9, the use of a morphine-sulfonamide on position six.

Houdi et al., *Pharmacol., Biochem. & Behavior* (March, 1996) disclosing morphine-6-sulfate esters and their analgesic character. This is the work of the present inventors.

Brown et al., *J. Pharm. Sci.* 74:821–24 (August, 1985) relates to the analgesic potencies of several morphine analogues with covalent modifications at carbons 3 and 6. Specifically, morphine-6-sulfate is disclosed.

Choonara et al., *J. Clin. Pharmacol.* 30:897–900 (December, 1990) describes the metabolism of morphine and the detection of morphine-3 and morphine-6-sulfate.

Oguri et al., *Eur. J. Pharmacol.* 102:229–35 (July, 1984) relates to the dependency of nalorphine-6-sulfate conjugates.

Hirano et al., *Chem. Pharm. Bull.* 39:2000–4 (August, 1991) relates to the synthesis and pharmacological activity of nalorphine-6-sulfate conjugates.

There is a need in the art for effective treatments for relieving pain in animals and humans. The present invention overcomes deficiencies in the prior art in providing new and effective treatments for pain, and other conditions whose symptoms are known to be alleviated with morphine compounds.

DISCLOSURE OF THE INVENTION

The present invention relates to morphine analogues, substituted with both a sulfate group at position six of the ring and an ester group at position three. The compounds are used as analgesics and for the treatment of pain.

More particularly the compounds selected from the group consisting of the following formulas I and II:

Formula I

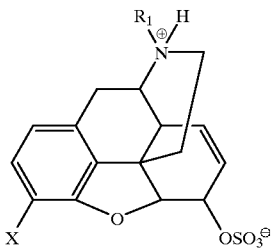

wherein X is selected from the group consisting of
—OR2,

and

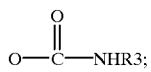

wherein R1 may be a straight or branched chain alkyl or alkenyl group having 1–5 carbon atoms;
wherein R2 is an alkyl having 1–3 carbon atoms, and
wherein R3 is H or n-alkyl or branched alkyl with 1–10 carbon atoms (preferably 4–8 carbon atoms), cycloalkyl, aralkyl, n-alkenyl or branched alkenyl with 1–10 carbon atoms, and n-alkynyl or branched alkynyl with 1–10 carbon atoms. R3 is preferably $OCH_3$, $OCOCH_3$, $OCOCH_2CH_3$, $OCOCH(CH_3)_2$, $OCOCH(CH_3)_3$ and OCO-phenyl.

Formula II

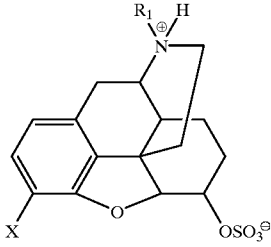

wherein X is selected from the group consisting of
—OR2,

and

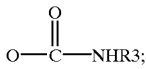

wherein R1 may be a straight or branched chain alkyl or alkenyl group having 1–5 carbon atoms;

wherein R2 is an alkyl having 1–3 carbon atoms, and wherein R3 is H or n-alkyl or branched alkyl with 1–10 carbon atoms, cycloalkyl, aralkyl, n-alkenyl or branched alkenyl with 1–10 carbon atoms (preferably 4–8 carbon atoms), and n-alkynyl or branched alkynyl with 1–10 carbon atoms. R3 is preferably selected from the group consisting of $OCH_3$, $OCOCH_3$, $OCOCH_2CH_3$.

The above and other objects of the invention will become readily apparent to those of skill in the relevant art from the following detailed description and figures, wherein only the preferred embodiments of the invention are shown and described, simply by way of illustration of the best mode of carrying out the invention. As is readily recognized the invention is capable of modifications within the skill of the relevant art without departing from the spirit and scope of the invention.

DESCRIPTION OF THE INVENTION

Figure 1:
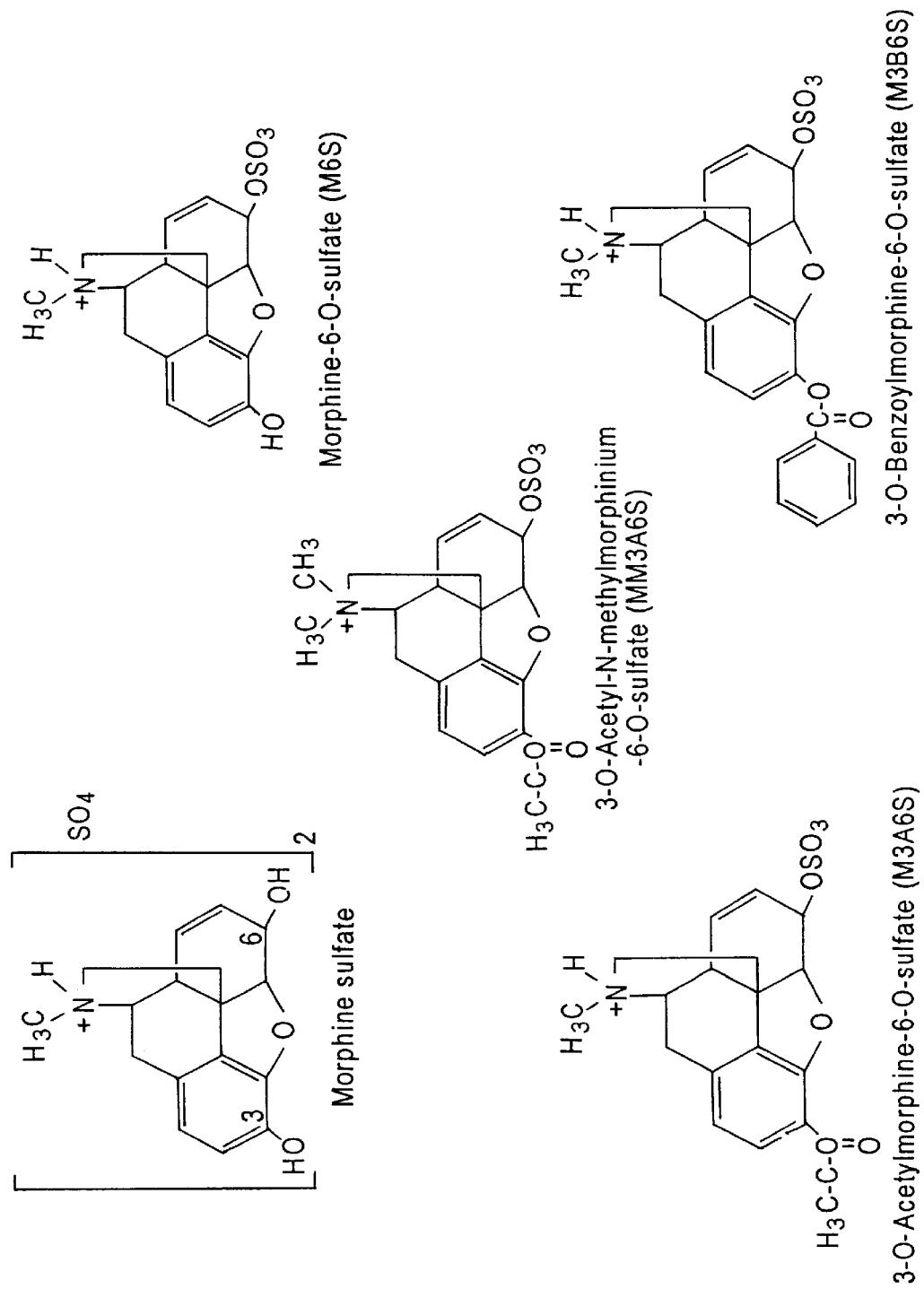
FIG. 1 shows structures of morphine and morphine-6-O-sulfate derivatives.

The present invention relates to 3-O-Acetylmorphine-6-sulfate compounds and their ester derivatives which are potent, centrally-acting morphine derivatives. The compounds are useful for the treatment of pain.

The following is a list of abbreviations which appear throughout the application.

| | |
|---|---|
| CNS: | Central Nervous System |
| GI: | Gastrointestinal |
| PETT: | Position emission transaxial tomography |
| ATP: | 5'-adenosine triphosphate |
| cAMP: | Cyclic 3',5'-adenosine monophosphate |
| MHP: | Mouse hot plate assay |
| UDPGA: | Uridine diphosphate glucuronic acid |
| M6S: | Morphine-6-O-sulfate |
| M3A6S: | 3-0-Acetylmorphine-6-0-sulfate |
| M3Pr6S: | 3-0-Propionylmorphine-6-0-sulfate |
| M3Ibu6S: | 3-0-Isobutyrylmorphine-6-0-sulfate |
| APS: | Adenosine 5'-sulfatophosphate |
| PAPS: | 3'-phosphoadenosine-5'-phosphosulfate |
| M3P6S: | 3-0-Pivaloylmorphine-6-0-sulfate |
| M3B6S: | 3-0-Benzoylmorphine-6-0-sulfate |
| DM3B6S: | 3-0-Benzoyl-7,8-dihydromorphine-6-0-sulfate |
| M6G: | Morphine-6-0-glucuronide |
| M3G: | Morphine-3-0-glucuronide |
| i.c.v.: | Intracerebroventricular |
| i.p.: | Intraperitoneal |
| CSF: | Cerebro-spinal fluid |
| DADL: | D-alanine D-leucine |
| DM: | 7,8-Dihydromorphine |
| DM6S: | 7,8-Dihydromorpihine-6-0-sulfate |
| MM3A6S: | 3-0-Acetyl N-methylmorphinium-6-0-sulfate |
| MM3B6S: | 3-0-Benzoyl N-methylmorphinium-6-0-sulfate |
| s.c.: | Sub-cutaneous |
| TLC: | Thin Layer chromatography |
| HETCOR: | Hetero-atom chemical shift correlation |
| COSY: | Homonuclear correlation |
| DEPT: | Distortionless enhancement by polarization transfer |
| FABMS: | Fast atom bombardment mass spectroscopy |
| RTF: | Rat Tail Flick |
| % MPE: | Percentage of maximum possible effect |
| % MPA: | Percentage of maximum possible analgesia |
| SDA: | Single dose suppression |
| PPt-W: | Precipitated Withdrawal |
| CP/MAS: | Cross polarization, magic angle spinning |
| SAR: | Structure-activity relationship |
| TMS: | Tetramethyl silane |
| ADTN: | 2-Amino-6,7-dihydroxytetrahydronaphthalene |

In view of the potent analgesia exhibited by the apparent structurallydissimilarmorphine-6-O-glucuronide (M6G) and morphine-6-O-sulfate (M6S) conjugates of morphine, the effect of structural modification of M6S on analgesic activity has been examined using the tail-flick test. Changes in the M6S structure were made that would affect the lipophilicity and polarity of the molecule. Subcutaneous (sc) and intracerebroventricular (icv) administration of equimolar doses of morphine, M6S, 3-O-acetylmorphine-6-O-sulfate (M3A6S), 3-O-benzoylmorphine-6-O-sulfate (M3B6S) and 3-O-acetyl-N-methylmorphinium-6-O-sulfate (MM3A6S) were employed.

M6S and M3A6S unexpectedly exhibited a longer duration of action and greater activity compared to morphine after Sc and icv administration. However, M3B6S and MM3A6S in a doses equimolar to that of morphine were found to be inactive after both Sc and icv administration. In addition, M3A6S showed the highest potency in inhibiting electrically stimulated guinea pig ileum followed by M6S and M3B6S. Moreover, both M6S and M3A6S displayed a greater affinity than that of morphine to mu and $kappa_3$ receptor sites in guinea pig brain homogenate.

In contrast, the non-analgesic compounds M3B6S and MM3A6S showed weak receptor binding ability compared to morphine. These results indicate that lipophilicity alone is not a determinant of analgesic activity in these novel morphine derivatives. These modified effects of morphine by the conjugations at the 3- and 6-position, appear to be due to their altered interactions with opioid receptors After examining the clinical activity of M6G in a group of cancer patients, it has been concluded that the analgesic effect of administered morphine is due mainly to metabolically formed M6G rather than to morphine itself [11]. Interestingly, the conjugate, morphine-6-O-sulfate (M6S) was shown to exhibit more potent and longer acting analgesia than morphine itself in mice [2]. On the other hand, M6S showed comparatively reduced competing potencies toward mu-receptors but enhanced delta-receptor affinity compared to parent compound morphine [10].

In view of the potent analgesia exhibited by the apparent structurally dissimilar 6-O-glucuronide and 6-O-sulfate conjugates of morphine, the effect of structural modification on antinociceptivity in the M6S molecule was examined. Of particular interest was the effect of increasing lipophilicity on activity by esterification of the 3-hydroxy group and the effect of increasing polarity by conversion of M6S to its N-methyl morphinium betaine (see FIG. 1).

As part of these structure-activity studies, the inventors report on the potent, centrally-acting antinociceptive activity of the morphine derivative, 3-O-acetylmorphine-6-O-sulfate, in the rat.

Tables 1-1–1-4

TABLE 1-1

INHIBITORY EFFECTS ($K_i$ VALUES) OF NEW COMPOUNDS ON THE BINDING OF
TRITIATED LIGANDS TO $\mu$-, $\delta$-, AND $\kappa$-SITES OF GUINEA-PIG BRAIN HOMOGENATES

| | $K_i$ (nM) | | | | | | |
|---|---|---|---|---|---|---|---|
| NIDA # | $\mu$ [$^3$H]DAMGO | $\delta$ [$^3$H]Cl-DPDPE | $\kappa_1$ [$^3$H]U69593 | $\kappa_2$ IC$_{50}$ (nM) | $\kappa_3$ [$^3$H]NalBzoH | $\sigma$ [$^3$H]3PPP | PCP [$^3$H]MK-801 |
| SUBMITTING CHEMIST: Peter Crooks | | | | | | | |
| 20,264 M3A6S | 0.8 ± 0 | 307.8 (1) | 1165 ± 184.55 | >10,000 | 5.5 ± 1.2 | — | — |
| 20,265 DM3A6S | 13.7 ± 0.55 | 325.3 ± 71.15 | >10,000 | >10,000 | 838.2 ± 743.6 | — | — |
| 20,266 M6S | 0.9 ± 0 | 18.0 ± 0.4 | 1192.0 ± 697 | >10,000 | 6.3 ± 0.3 | — | — |
| 20,267 DNaM6S | 1.5 ± 0.25 | 18.8 ± 3.35 | 3128.9 ± 368.25 | >10,000 | 7.0 ± 0.2 | — | — |
| 20,268 M3S | 101.4 ± 0.7 | >10,000 | >10,000 | >10,000 | 1694.4 ± 287.25 | — | — |
| 20,269 MM3A6S | 34.2 ± 12.1 | 841.8 ± 189.25 | >10,000 | >10,000 | 400.1 ± 58.4 | — | — |
| 20,270 M3Pr6S | 0.6 ± 0.15 | 40.0 ± 1.9 | 251.7 ± 38.55 | >10,000 | 19.9 ± 16 | — | — |
| 20,271 M31BU6S | 19.8 ± 0.6 | 584.2 ± 28.75 | 4558.0 ± 229.15 | >10,000 | 266.3 ± 68.5 | — | — |
| 20,272 M3P6S | 0.7 ± 0.15 | 15.2 ± 4.25 | 1940.5 ± 198 | >10,000 | 11.2 ± 3.15 | — | — |
| 20,273 M3B6S | 36.9 ± 1.3 | 599.5 ± 1.50 | >10,000 | >10,000 | 513.3 ± 14.7 | — | — |
| 20,274 MM3B6S | 443.8 ± 169.1 | >10,000 | >10,000 | >10,000 | >10,000 | — | — |
| 20,275 DM3B6S | 61.8 ± 13.15 | 1598.3 ± 422.45 | >10,000 | >10,000 | 822.2 ± 83.05 | — | — |
| 20,276 C6S | 38.7 ± 7.95 | 414.0 ± 140.45 | >10,000 | >10,000 | 454.6 ± 224.2 | — | — |
| 20,277 DHC6S | 195.9 ± 57.7 | 1151.7 ± 183.7 | >10,000 | >10,000 | 759.7 ± 83.4 | — | — |

TABLE 1-2

STANDARDS
INHIBITORY EFFECTS ($K_i$ values) OF OPIOIDS ON THE BINDING OF
TRITIATED LIGANDS TO $\mu$-, $\delta$-, AND $\kappa$- SITES OF GUINEA-PIG BRAIN HOMOGENATES

| Cold Ligand | $\mu$ [$^3$H]DAMGO | $\delta$ [$^3$H]Cl-DPDPE | $\kappa_1$ [$^3$H]U69,593 | $\kappa_2$ IC$_{50}$ (nM) | $\kappa_3$ [$^3$H]NalBzoH |
|---|---|---|---|---|---|
| Naloxone-HCl | 1.5 ± 0.02 | 19.8 ± 0.7 | 3.8 ± 0.9 | 442.5 ± 22 | 9.6 ± 0.35 |
| (+)Naloxone-HCl | >10,000 | >10,000 | >10,000 | >10,000 | >10,000 |
| Naltrexone-HCl | 0.4 ± 0.05 | 6.5 ± 1.3 | 0.6 ± 0.1 | 230.0 ± 9.2 | 3.8 ± 0.3 |
| β-FNA-HCl | 0.4 ± 0.05 | 7.7 ± 0.4 | 0.9 ± 0.05 | 66.5 ± 14.8 | 0.8 ± 0 |
| β-CNA-(HCl)$_2$ | 0.7 ± 0.05 | 4.8 ± 0.14 | 0.4 ± 0.1 | 208.5 ± 11.8 | 1.6 ± 0.05 |
| DPDPE-Cl | 180.0 ± 1.2 | 0.3 ± 0.07 | >10,000 | >10,000 | 1,028.0 ± 219 |
| DPDPE-OH | >10,000 | 2.8 ± 0.4 | >10,000 | >10,000 | >1,000 |
| DSLET-OH | 20.6 ± 3.6 | 0.5 ± 0 | >10,000 | >10,000 | >1,000 |
| DTLET-OH | 14.7 ± 1.4 | 0.3 ± 0 | >10,000 | >10,000 | 127.2 ± 19 |
| DADLE-OH | 3.2 ± 0.05 | 0.3 ± 0 | >10,000 | >10,000 | 692. ± 7.6 |
| Leu-Enkephalin | 21.7 ± 1.4 | 1.6 ± 0.5 | >10,000 | >10,000 | 1,672.8 ± 523 |
| Met-Enkephalin | 6.9 ± 1.5 | 1.1 ± 0.2 | 4,467.2 ± 865 | >10,000 | 277.3 ± 29 |
| Dynorphin(1-9)-OH | 86.3 ± 6.5 | 1.0 ± 0.2* | 1.4 ± 0.4 | 324.5 ± 10.4 | 20.2 ± 3.0 |
| Naltrindole | 0.2 ± 0.01 | 0.09 ± 0 | 7.8 ± 0.1 | 539.5 ± 43 | 12.4 ± 3.0 |
| ICI 174, 864-OH | >10,000 | 194.7 ± 9.1 | >10,000 | >10,000 | >10,000 |
| BNTX | 1.9 ± 0.5 | 4.2 ± 0 | 7.1 ± 1.7 | 822.5 ± 3.5 | 3.5 ± 0.1 |

*Experiment was done with [$^3$H]DPDPE

TABLE 1-3

STANDARDS
INHIBITORY EFFECTS ($K_i$ values) OF OPIOIDS ON THE BINDING OF
TRITIATED LIGANDS TO $\mu$, $\delta$, AND $\kappa$-SITES OF GUINEA-PIG BRAIN HOMOGENATES

| | $K_i$ (nM) | | | | |
|---|---|---|---|---|---|
| Cold Ligand | $\mu$<br>[$^3$H]DAMGO | $\delta$<br>[$^3$H]Cl-DPDPE | $\kappa_1$<br>[$^3$H]U69,593 | $\kappa_2$<br>$IC_{50}$ (nM) | $\kappa_3$<br>[$^3$H]NalBzoH |
| NTB | 6.5 ± 1.1 | 0.06 ± 0 | 10.2 ± 2.4 | 406.0 ± 42 | 7.5 ± 1.0 |
| U69,593 | 692.0 ± 97 | 1,358.4 ± 118* | 0.7 ± 0.05 | 6,763.0 ± 417 | 1,098.6 ± 0.2 |
| UPHIT | 1,950.0 ± 106 | >10,000 | 10.7 ± 0.45 | 318.6 ± 92 | 2,524.7 ± 695 |
| U50,488H | 294.0 ± 49 | >10,000* | 0.2 ± 0.05 | 307.5 ± 61.5 | 133.2 ± 31 |
| (−)EKC | 0.4 ± 0.04 | 2.0 ± 0.07 | 0.1 ± 0 | 25.2 ± 0.75 | 3.9 ± 1.0 |
| (+)EKC-sulfonate | 1.1 ± 0.05 | 2.6 ± 0.30* | 1.8 ± 0.85 | 133.0 ± 0.9 | 5.3 ± 3.0 |
| (−)Bremazocine | 0.1 ± 0 | 0.3 ± 0.07 | 0.1 ± 0.03 | 2.2 ± 0.1 | 0.1 ± 0 |
| (+)Bremazocine | 0.1 ± 0 | 0.7 ± 0.20 | 0.1 ± 0.02 | 11.2 ± 0.9 | 0.1 ± 0 |
| Etorphine-HCl | 1.5 ± 0.35 | 0.7 ± 0.07 | 0.8 ± 0.20 | 26.1 ± 6.8 | 0.4 ± 0.15 |
| Nor-BNI (HCl)$_2$ | 8.3 ± 1.2 | 6.3 ± 0.60 | 0.3 ± 0.10 | 37.5 ± 3.5 | 15.0 ± 1.6 |
| Dynorphin (1-8) | 6.8 ± 0.2 | 1.5 ± 0.70* | 65.0 ± 10.8 | 1,762.0 ± 284 | 12.9 ± 0.9 |
| Dynorphin (1-11)-OH | 2.3 ± 0.5 | 1.8 ± 0.20* | 0.1 ± 0 | 13.3 ± 0.5 | 23.1 ± 9.0 |
| Dynorphin (1-13)-NH$_2$ | 3.5 ± 0.15 | 7.7 ± 1.0* | 0.3 ± 0.1 | 24.6 ± 1.8 | 4.1 ± 1.4 |
| Dynorphin (1-13)-OH | 3.3 ± 0.1 | 16.3 ± 0.9 | 0.4 ± 0.1 | 180.0 ± 1.8 | 15.4 ± 1.0 |
| Dynorphin (1-17)-OH | 8.1 ± 0.2 | 5.8 ± 0.8 | 1.7 ± 0 | 29.5 ± 0.7 | 5.1 ± 1.1 |
| Dynorphin B-OH | 5.5 ± 0.2 | 4.2 ± 0.25* | 0.9 ± 0.1 | 70.0 ± 7.3 | 14.2 ± 3.3 |

*Experiment was done with [$^3$H]DPDPE

TABLE 1-4

STANDARDS
INHIBITORY EFFECTS ($K_i$ values) OF OPIOIDS ON THE BINDING OF
TRITIATED LIGANDS TO $\mu$-, $\delta$-, AND $\kappa$-SITES OF GUINEA-PIG BRAIN HOMOGENATES

| | $K_i$ (nM) | | | | |
|---|---|---|---|---|---|
| Cold Ligand | $\mu$<br>[$^3$H]DAMGO | $\delta$<br>[$^3$H]Cl-DPDPE | $\kappa_1$<br>[$^3$H]U69,593 | $\kappa_2$<br>$IC_{50}$ (nM) | $\kappa_3$<br>[$^3$H]NalBzoH |
| (−) Cyclazocine | 0.1 ± 0.0 | 0.6 ± 0.05* | 0.1 ± 0.02 | 17.3 ± 3.0 | 0.2 ± 0 |
| (+) Cyclazocine | 659.0 ± 28 | >10,000* | 383.4 ± 53 | >10,000 | 785.6 ± 121 |
| (−) SKF 10,047-HCl | 0.7 ± 0.1 | 3.8 ± 0* | 0.3 ± 0.05 | 132.5 ± 2.0 | 1.5 ± 0.6 |
| (+) SKF 10,047-HCl | 2,117.0 ± 66 | >10,000* | 2,889.0 ± 140 | >10,000 | >1,000 |
| (−) Pentazocine-succinate | 5.7 ± 0.9 | 32.7 ± 3.15* | 4.4 ± 0.1 | 423.5 ± 171 | 12.4 ± 1.5 |
| (+) Pentazocine-succinate | 595.0 ± 1.05 | 3,480.0 ± 441* | 205.7 ± 57 | 5,270.5 ± 1,402 | 419.8 ± 21 |
| NalBzoH | 0.2 ± 0 | 1.4 ± 0.13 | 0.4 ± 0.1 | 66.5 ± 12 | 0.3 ± 0.07 |
| (−) WIN 44,441 methane sulfonate | 0.1 ± 0.03 | 0.9 ± 0.07* | 0.2 ± 0 | 6.1 ± 0.3 | 0.3 ± 0.05 |
| β-Endorphin-OH | 2.3 ± 0.5 | 1.6 ± 0.45* | 43.5 ± 4.1 | 2,052.0 ± 812 | 14.5 ± 0.4 |
| Ibogaine | 3,888.9 ± 33 | >10,000 | 4,243.0 ± 523 | >10,000 | 1,088.0 ± 32 |
| PCP-HCl | >10,000 | >10,000* | >10,000 | >10,000 | >10,000 |
| TCP-HCl | 2,199.0 ± 219 | >10,000* | 2,036.9 ± 260 | >10,000 | >10,000 |
| DTG-OH | 1,885.0 ± 373 | >10,000* | 1,033.8 ± 264 | >10,000 | 3,487.5 ± 279 |
| (+) MK-801-OH | >10,000 | >10,000* | >10,000 | >10,000 | — |
| (+) 3-PPP-HCl | 3,448.4 ± 77 | >10,000* | 388.0 ± 110 | >10,000 | 782.1 ± 48 |

*Experiments were done with [$^3$H]DPDPE

EXAMPLE 1

Animals and Surgery

The assessment of analgesic response by the tail flick test was carried out on male sprague-Dawley rats (Harlan Industrial, Indianapolis, Ind.) weighing 270–310 g at the time of experimentation. Rats were housed individually in a room maintained at 24° C. (constant temperature and humidity) with a 12 h light-dark cycle for one week before use in the studies. Food and water were available ad libitum.

Rats were anesthetized using equithesin (3 ml/kg) during the duration of the surgery. A stainless steel guide cannula (Plastic Products, Roanoke, Va.) was implanted over the left lateral cerebral ventricle. The rat was positioned in a stereotaxic frame (David Kopf); stereotaxic coordinates were 0.8 mm posterior to the bregma, 1.4 mm lateral to the midline, and 3.2 mm below the skull. The guide cannula was secured permanently with skull screws and dental acrylic (Lang Dental Manufacturing Co., Chicago, Ill.). A 28-gauge dummy cannula was kept in the implanted cannula, except during intracerebroventricular (icv) injections. The rats were allowed to recover from surgery for 3–4 days prior to the experiments.

EXAMPLE 2

Antinociceptive Testing

The antinociceptive activity of the morphine analogs. was evaluated by thermal stimuli, utilizing the tail-flick test of D'Amour and Smith [4]. The radiant heat was focused on the tail tip of a male Sprague-Dawley rat, and the heat intensity was adjusted so that a control animal flicked its tail within 1.7–2.6 seconds of exposure. In order to prevent tissue damage in drug-treated animals, a latency cut-off time of 8 seconds was employed. Each rat served as its own control, since the latency to response was measured both before and after drug administration. Rats were acclimated to the tail flick test 3 times before the actual experiment was run. Measurements of analgesia, or antinociception were expressed as:

$$\% \text{ Maximum Possible Response (\% MPR)} = \frac{\text{Post-drug Latency} - \text{Base line Latency}}{\text{Cut-off Time (8.0 s)} - \text{Base line Latency}} \times 100$$

Experimental Protocol

On the day of the experiment, rats were placed in a restrainer for 15 min. before actual testing began. Four baseline trials were carried out before drug administration, one every 5 min. Then, rats were removed briefly from their restrainers for sc administration of drugs. The drug was dissolved or suspended (sonicated and vortexed) in sesame seed oil (Fisher Scientific Co.) prior to injection (1 ml/kg). Five mg/kg (0.0175 mmole) of morphine as free base was used. Equimolar doses of morphine derivatives to that of morphine were as follows: M6S (6.4 mg/kg); M3A6S (7.1 mg/kg); M3B6S (8.2 mg/kg); and MM3A6S (7.4 mg/kg). The tail-flick procedure was then continued.

For icv administration, test compounds were dissolved in saline prior to administration. On the day of the experiment, 30 minutes before drug administration, animals were handled briefly in order to lower a drug-filled injector through the guide cannula into the lateral ventricle. The injector consisted of a segment of stainless steel tubing connected to a Hamilton Syringe by PE20 tubing. The rats were then placed in restrainers for 15 minutes prior to actual testing. Four base-line trials were done, one every 5 minutes, before drug administration. Micro-injection of the drug solution (each treatment consisted of 4 ul of solution per rat) was made over one minute, using a pre-programmed syringe pump (Tracor, Atlas, Houston, Tex.). The tail-flick procedure was then continued at 3 minute intervals for the first 30–45 minutes and then at longer time intervals (15 minutes-30 minutes) until analgesia was abolished. An 8 second cut-off time was used to prevent damage to the tail. For icv drug administration, 2 doses of morphine were used; low dose morphine 0.236 µg/rat (0.83 pmole µmole/rat as free base), high dose morphine 23.6 µg/rat (83 pmole/rat). Doses of morphine derivatives administered icv were equimolar to the low dose of morphine and were as follows: M6S (0.22 µg/kg); M3A6S (0.25 µg/kg); M3B6S (0.29 µg/kg); and MM3A6S (0.26 µg/kg).

Successful icv injection was confirmed by monitoring the movement of a small air bubble over a calibrated distance in the PE20 tubing during the drug administration. Additionally, at the conclusion of the experiment, each icv treatment was verified by examining the cerebral ventricle after a 4 µl fast green dye injection over one minute, into the deeply anesthetized rat.

EXAMPLE 3

Receptor Binding

Hartley guinea pigs were decapitated and their brains were quickly removed and weighed. The brains were then homogenized in 50 mM Tris HCl, buffer pH 7.7, using a Polytron (~25 ml/brain). The homogenate was centrifuged at 40,000×g for 15 min, rehomogenized and centrifuged. The final pellet was resuspended in Tris HCl, pH 7.7, at a final concentration of 6.67 mg original wet weight of tissue per ml, except for tissue prepared for ($^3$H)NalBzoH (naloxone benzoylhydrazone, NIDA) binding which was resuspended in buffer containing 5 mM EDTA.

The following radioligands (~1 nM) were used to label the receptor binding sites indicated in parentheses: ($^3$H) DAMGO [D-Ala$^2$,N-Me-Phe$^4$,Gly-ol$^5$]-enkephalin, (mu), ($^3$H)DPDPE [D-Pen$^{3,5}$-enkephalin], (delta), ($^3$H)U69,593 (kappa$_1$), ($^3$H)NalBzoH (kappa$_3$). The guinea pig brain suspension (1.8 ml) was incubated in 50 mM Tris HCl. Nonspecific binding was determined by incubating in the presence of 1 µM of the "cold" unlabeled counterpart of each labeled ligand, except that 10 µM±NalBzoH was used for the kappa$_3$ assay. The samples were then filtered through glass fiber filters on a 48-well Brandel cell harvester. The filters were washed 3 times with 3 ml of buffer. Filters were incubated overnight with 5 ml of scintillation cocktail before counting.

Results are reported in terms of IC$_{50}$ (concentration of test compound that produces 50% inhibition of labeled ligand binding). The K$_i$ (Inhibitory Dissociation Constant) values are derived from the following equation: K$_i$=IC$_{50}$/1+[L]/Kd. The Kd values were obtained by computer analysis of detailed self-inhibition curves for each of the labeled ligands (L), using the curve-fitting program LIGAND.

EXAMPLE 4

In Vitro Functional Assays a. Guinea Pig Ileum (GPI) Preparation Male Hartley guinea pigs (350–400 g wt) were decapitated and their small intestines were removed; about 20 cm of the terminal ileum was discarded. The longitudinal muscle with the myenteric plexus attached was gently separated from the underlying circular muscle by the method of Paton and Vizi [13]. The muscle strip was mounted in an 8 ml water-jacketed organ bath containing Krebs-bicarbonate solution of the following composition: 118 mM NaCl, 2.5 mM CaCl$_2$, 4.7 mM KCl, 25 mM NaHCO$_3$, 1.2 mM KH$_2$PO$_4$, 1.2 mM MgSO$_4$ and 11.5 mM glucose. The tissues were kept at 37° C. and bubbled with 5% CO$_2$ in oxygen. An initial tension of 0.6–1.0 g was applied to the strips. The muscle strip was stimulated for 60 min before the start of each experiment.

Field electrical stimulation was delivered through platinum wire electrodes positioned at the top and bottom of the organ bash and kept at a fixed distance apart (3.5 cm). The upper electrode is a ring of 4 mm diameter. The parameters of rectangular stimulation were as follows: supramaximal voltage, 1 msec impulse duration at a rate of 0.1 Hz. A Grass S-88 electrostimulator was used for stimulation. The electrically induced twitches were recorded using an isometric transducer (Metrigram) coupled to a Grass 7D multichannel polygraph.

EXAMPLE 5

Mouse Vas Deferens (MVD) Preparation

The vas deferens from Swiss-Webster mice (30–35 g) were prepared as described by Hughes et al. [6]. The tissues were mounted on organ bath containing 8 ml of magnesium free Krebs solution at 31° C., which was bubbled with a mixture of oxygen and carbon dioxide (95:5). An initial tension of 150–200 mg was used.

Field stimulation parameters were modified slightly from those of Hughes et al. [6] as described by Ronai et al. (17); paired shocks of 100 msec delay between supramaximal rectangular pulses of 1 msec delay between supramaximal rectangular pulses of 1 msec duration were delivered at a rate of 0.1 Hz. A Grass S-88 electrostimulator was used for stimulation. The contractions were recorded using an isometric transducer (Metrigram) coupled to a Gras 7D multichannel polygraph.

The agonist potencies of test compounds were determined from concentration-response curves and characterized by their $IC_{50}$ values. $IC_{50}$ is defined as the concentration of the agonist that causes 50% inhibition of the electrically induced contractions. In order to determine the site(s) at which the agonists acted, assays were conducted in the presence of site-selective antagonists. A shift of the dose-response curve to the right is indicative of activity at the antagonist bound site. One hundred nM CTAP (D-Phe-Cys-Tyr-D-Trp-Arg-Thr-Pen-Thr-$NH_2$) and 20 nM nor-BNI [nor-binaltorphimine] were added to the GPI preparation to selectively block mu (7) and kappa (15) receptors, respectively; 1 nM naltrindole was added to the MVD preparation to selectively block delta receptors (16). This activity was characterized by dose ratios (DR). DR was calculated from the following equations:

$$DR = \frac{IC_{50} \text{ in the presence of antagonist}}{IC_{50} \text{ in the absence of antagonist}}.$$

EXAMPLE 5

Chemicals

The compounds utilized in this study were: morphine sulfate salt (Mallinckrodt Inc., Paris, Ky.), morphine-6-O-sulfate (M6S), 3-O-acetyl morphine-6-O-sulfate (M3A6S), 3-O-benzoylmorphine-6-O-sulfate (M3B6S), and 3-O-acetyl-N-methylmorphinium-6-O-sulfate (MM3A6S).

The sulfate esters were synthesized in our laboratories and their preparation is reported below. See FIG. 1 for the structural formula of these compounds.

Morphine sulfate pentahydrate salt was purchased from Mallinckrodt (Paris, Ky.). All other reagents were purchased from Aldrich (Milwaukee, Wis.) and Fisher Scientific Co. (Pittsburgh, Pa.). Solvent pyridine was dried over calcium hydride, immediately before use. Whatman Diamond silica gel analytical TLC plates (250 μm.) (Whatman International, Maidstone, England) with fluorescent indicator were used. Reactions followed by analytical TLC, were detected under ultraviolet light (254 nm) using a Model WG-54 MINERALIGHT lamp (Ultra-Violet Products, Inc., San Gabriel, Calif.). Evaporation of samples under reduced pressure was accomplished utilizing a Buchi Rotavapor-EL (Brinkmann Instruments, Westbury, N.Y.) operating under a vacuum supplied by either a water aspirator or a Gast pump. Evaporation of solvent at high vacuum (5–10 mm Hg) was accomplished using a Welch DuoSeal vacuum pump, model no. 1400 (Welch Vacuum Technology, Inc., Skokie, Ill.). Hydrogenation was carried out at 10–15 psi using a Parr pressure reaction apparatus (Parr Instrument Co., Inc., Moline, Ill.). Melting points were determined on a Fisher-Johns melting point apparatus (Fisher Scientific Co., Fairlawn, N.J.) and are reported uncorrected. Elemental analyses were performed by Atlantic Microlabs, Atlanta, Ga.

Nuclear magnetic resonance (NMR) spectra were recorded in DMSO-d6 at 200 MHz, 400 MHz or 500 MHz on a Varian Gemini-200, Varian VXR-400 or Varian VXR-500 spectrometer. Chemical shifts are expressed in o-values (ppm) downfield from tetramethylsilane (TMS) as internal standard and signals are defined as singlet (s), broad singlet (bs), doublet (d), triplet (t), quartet (q) and multiplet (m). Whenever necessary to help in unequivocally assign specific carbon and proton chemical shifts, 13C-DEPT (Distortionless enhancement by polarization transfer) 1H-COSY (homonuclear correlation) and 1H, 13C-HETCOR (heteroatom chemical shift correlation) spectra were recorded. Fast atom bombardment masx spectra (FAB ms) were determined on a KRATOS concept IH high resolution mass spectrometer. The mass spectrometer was operated at a 6 kV accelerating potential. The fast atom bombardment (FAB) gun is an Ion Tech model BIINF saddle field force that operates at 6–8 kV using xenon gas. Data was recorded using Kratos DS 90 software on a DG 30 computer system. Spectra were acquired at 1 sec/decade or 3 sec/decade and calibration was performed using CsI. Samples were dissolved in glycerol or a 10% glycero-U-methanol-water mixture and a 1 μl sample was placed on the FAB probe tip for subsequent analysis.

Energy minimization calculations were carried out using a CHARMm software program (Brook, et al., 1983) for which interactive access is provided by QUANTA (POLYGEN Corporation). All calculations were carried out on a Silicon Graphics Iris 4D/70GT Work station. CHARMm is a general and flexible software application for modeling the structure and behavior of molecular systems. A variety of systems, from isolated small molecules through solvated complexes of large biological macromolecules can be simulated.

CHARMm uses empirical energy functions to describe the forces on atoms in molecules. These functions, plus the parameters for the functions, constitute the CHARMm force field. CHARMm uses these functions to rapidly calculate conformational energies, local minima, barriers to rotation, energy surfaces and time dependent dynamic behavior.

3-O-Acetylmorphine

A modification of the method of Welsh (1954) was utilized. Morphine free base (1 am, 3.50 mmol) was suspended in saturated sodium bicarbonate solution (50 ml), and to the stirred suspension was added drop-wise an excess of acetic anhydride (1 ml, 10.6 mmol). The resulting solution was extracted with chloroform (6×10 ml) and the combined organic extracts were dried over anhydrous magnesium sulfate. Following filtration the solvent was removed by rotary evaporation under reduced pressure to afford 1.14 gm (100%) of 3O-acetylmorphine as a glassy white amorphous solid. The product was homogeneous by TLC ($CHCl_3$:MeOH (9:1), $R_f$=0.85). Elemental Analysis Calcd. for $C_{19}H_{21}NO_4$: C, 69.73, H, 6.42; N, 4.28. Found: C, 69.71;, H,6.40; N, 4.32.)

3-O-Benzoylmorphine

Morphine free base (500 mg., 1.75 mmol) was suspended in saturated sodium bicarbonate solution (50 ml) To the continuously stirred suspensions was added a molar equivalent of benzoic anhydride (396.89 ma, 1.75 mmol.), and the reaction was left to stir overnight at ambient temperature. The resulting solution was extracted with chloroform (6×10 ml) and the combine organic extracts dried over anhydrous magnesium sulfate and filtered. The solvent was then removed by rotary evaporation under reduced pressure to afford 0.520 gm (76.4%) of 3-O-benzoylmorphine as a colorless, amorphous solid, homogeneous by TLC ($CHCl_3$MeOH(9:1), $R_f$=0.8). Elemental Analysis: Calcd. for ($C_{24}H_{23}NO_4$: C, 74.04; H, 5.91; N, 3.60. Found: C, 74.11; H, 5.91; N, 3.63.

3-O-Pivaloylmorphine

The procedure employed was similar to the one used for preparing the 3-O-acetyl ester of morphine, except that to the continuously stirred suspension of morphine free base (500 ma,1.75 mmol.) an excess of pivalic anhydride (600~1, 2.95 mmol.) was added. This procedure afforded 0.550 gm (85.2%) of the 3-O-,Pivaloyl derivative of morphine as an off-white glassy solid, which was homogeneous by TLC (CHCl$_3$:MeOH (9:1), R$_f$=0.75). Elemental Analysis: Calcd. for C$_{22}$H$_{29}$NO$_4$: C, 71.16; H, 7.32; N, 3.77. Found: C, 71.06; H, 7.30; N, 3.80.

3-O-Propionylmorphine

The procedure employed was similar to the one utilized for obtaining the 3-O-acetyl ester of morphine, except that to the continuously stirred suspension of morphine free base (300 ma, 1.05 mmol.) an excess of propionic anhydride (600 µl, 4.68 mmol.) was added. This procedure afforded 0.357 gm. (99%) of the 3-O-propionyl ester of morphine as a colorless solid, homogeneous by TLC (CHCl$_3$:MeOH (9:1), R$_f$=0.8). Elemental Analysis: Calcu. for C$_{20}$H$_{23}$NO$_4$: C, 70:38; H, 6.75; N, 4.11. Found: C, 70.40; H, 6.79; N, 4.01.

3-O-Isobutyrylmorphine

The procedure employed was similar to the one utilized for obtaining the 3-O-acetyl ester of morphine, except that to the continuously stirred suspension of morphine free base ( 310 mg., 1.09 mmol. ) an excess of isobutyric anhydride was added. This procedure afforded 0.190 am. (49.1%) of the 3-O-isobutyryl ester of morphine ax a colorless solid, homogeneous by TLC (CHCl$_3$:MeOH (9:1), R$_f$=0.8). Elemental analysis: Calcd. for C$_{21}$H$_{25}$NO$_4$: C, 70.99; H, 7.04; N, 3.94. Found: C, 71.01; H, 7.06; N, 4.00.

7,8 Dihydromorphine

To morphine free base (3 am, 10.5 mmol.) dissolved in absoTute ethanol (150 ml) palladium-on-activated carbon (5~o) (1 am., 50 p.s.i.) was added. Reduction was carried out overnight (12–14 hours), in a Parr hydrogenator at ambient temperature. After confirmation of the quantitative conversion to 7,8-dihydromorphine by TLC, the ethanolic solution was filtered over Celite. The organic solvent ethanol was removed by rotary evaporation at reduced pressure, to afford 2.93 am. (97.2%) of dibydromorphine as an off-white glassy solid, homogeneous by TLC (CHCl$_3$:MeOH (9:1), R$_f$=0.2). Elemental Analysis Calcd. for C$_{17}$H$_{21}$NO$_3$:C, 71.08; H, 7.32; N, 4.88. Found: C, 71.11; H, 7.34; N, 4.91.

3-O-Acetyl-7.8-dihydromorphine

The procedure employed was similar to the one utilized for obtaining the 3-O-acetyl ester of morphine, except that to the continuously stirred suspension of the 7,8-dihydromorphine free base (2.93 am, 10.3 mmol.) an excess of acetic anhydride (3 ml, 31.8 mml) was added. This procedure afforded 2.74 gm (80.9¢Yo) of the 3-O-acetyl ester of 7,8-dihydromorphine as a glassy off-white solid, homogeneous by TLC (CHCl$_3$:MeOH (9:1), R$_f$=0.45). Elemental analysis: Calcd. for C$_{19}$H$_{23}$NO$_4$: C, 69.30, H, 6.99; N, 4.26. Found: C, 69.32; H, 7.02; N, 4.32.

3-O-Benzoyl-7,8-dihydromorphine 7,8-Dihydromorphine free base (200 mg, 0.70 mmol.) was suspended in saturated sodium bicarbonate solution (30 ml.). To the continuously stirred suspension a molar equivalent of benzoic anhydride (157.65 ma, 0.70 mmol.) was added, and the reaction left overnight (12–14 hours.) at ambient temperature. With time the resultant product precipitated out as a colorless white powder. The mixture was filtered to afford 1.87 mg (68.5%) of the 3-O-benzoyl derivative of 7,8-dihydromorphine, homogeneous by TLC (CHCl$_3$:MeOH (9:1), R$_f$=0.5). Elemental Analysis: Calcd. for C$_{24}$H$_{25}$NO$_4$: C, 73.66; H, 6.39; N, 3.58. Found: C, 73.71; H, 6.42; N, 3.61.

3-O-Acetyl-N-methylmorphinium Iodide

To 3-O-acetylmorphine (200 mg, 0.61 mmol) dissolved in dichloromethane (3 mls) at 0° C. over nitrogen, was added a 10% molar excess of iodomethane (41.9 µl, 0.67 mmol.). The reaction mixture was continuously stirred at ambient temperature overnight (12–14 hours.). The reaction afforded 196 mg (68.3%,) of the precipitated clean product which after filtration and repeated dichloromethane washes, was obtained as a colorless powder. M.P.: >300° C.

3-O-Acetylmorphine-6-O-sulfate Zwitterion

3-O-Actetylmorphine (3.25 gm, 0.01 mole) was dissolved in dry pyridine (dried over CaH$_2$) (8.5 ml). To the resultant solution, a 2.26 molar excess of the pyridine:SO$_3$ complex (3.575 gm, 0.022 moles was added) The reaction mixture was kept under nitrogen and stirred at 55° C. (oil bath) for three and a half hours. After quantitative completion of the reaction, as indicated by the TLC [Propanol: Chloroform: Methanol: Water (2:2:1:0.4), R$_f$0.2], the resultant slurry was dissolved in ice-cold distilled water (20 ml). The aqueous solution was then extracted with chloroform (6–10 ml), whereupon the 6-O-sulfate derivative, in its zwitterionic form precipitated from the aqueous solution as a colorless solid. Subsequent filtration and several washings with cold water afforded 2.584 gms (63.5%) of the required product. Recrystallization of the final product by dissolving in hot water followed by slow cooling resulted in the formation of fine reed-shaped crystals of the 6-O-sulfate derivative, m.p. 280–284° C. (dec.), MS (neg-FAB), m/z 406 (M–H). Elemental Analysis: Calcd. for C$_{19}$H$_{21}$O$_7$NS.1/3 H$_2$O: C, 55.20; H, 5.12; N, 3.44; S, 7.78. Found: C, 55.05; H, 5.22; N, 3.31; S, 7.55.

3-O-Acetyl-7,8-dihydromorphine-6-O-sulfate Zwitterion

3-O-Acetyl-7,8-dihydromorphine (2.74 gm,0.008 mole) was dissolved in dry pyridine (dried over CaH$_2$) (8 ml) to the resultant solution, a 2.26 molar excess of pyridine: SO$_3$ complex (2.996 gm, 0.019 mole) was added. The reaction mixture was stirred at 55° C. (in an oil bath) under nitrogen for two and a half hours. After quantitative completion of the reaction, as indicated by the TLC [Propanol: Chloroform: Methanol: Water (2:2:1:0.4), R$_f$=0.2], solvent pyridine was removed from the reaction mixture under high vacuum. The resultant pale brown powder was dissolved in distilled water (15 ml). Methanol (5 ml) was then added to the aqueous solution, whereupon, an offwhite precipitate developed. The resultant precipitate was filtered. Methanol (30 ml) was added to the filtered residue and the resulting suspension was stirred and sonicated for 10–15 minutes. Subsequent filtration afforded 1.473 gm (45%) of the required product as an off-white powder. Recrystallization of the final product from a water/methanol mixture yielded pale yellow rod shaped crystals of the 6-O-sulfate derivative as the zwitterion, m.: >300° C. (dec.), MS (neg-FAB) m/z 408 (M–H). Elemental analysis: Calcd. for C 1gH23NO7S: C, 55.73; H, 5.66; N, 3.42; S, 7.83; Found: C, 55.57; H,5.70; N, 3.48; S, 7.83.

3-O-Benzoylmorphine-6-O-sulfate Zwitterion

The procedure employed was similar to the one utilized for obtaining the 6-O-sulfate ester of 3-O-acetyl-morphine The procedure afforded 54 mg (44.8%) of the colorless solid product from 100 mg of 3-O-benzoylmorphine (0.26 mmole) . TLC [Propanol:Chloroform Methanol:Water (2:2:1:0.4), $R_f$=0.35] m.p.: 265–269° C. (dec. ), MS (neg-FAB) m/z 468 (M−H). Elemental analysis: Calcd. for $C_{24}H_{23}NO7S$. 1/2H2O: C, 59.12; H, 4.96; N, 2.87; S, 6.57. Found: C, 59.09; H, 5.18; N, 3.11; X, 7 26.

3-O-Propionylmorphine-6-O-sulfate Zwitterion

The procedure employed was similar to the one used for obtaining the 6-O-sulfate ester of 3-O-acetylmorphine This procedure afforded 205 mg (44.2%) of the colorless solid product from 377 mg (1.10 mole) of 3-O-propionylmorphine. TLC (Chloroform: Methanol: Water (2:1:0.5), Rf=0.4), m.p.: 230–235° C. (dec.), MS (pos-FAB) z 422 (M+H)+. Elemental analysis: Calcd. for $C_{20}H_{23}NO7S$: C, 55.80; H, 5.62 N, 3.25; S, 7.45; Found; C, 55.85; H, 5.61; N, 3.24; s, 7.51.

3-O-Isobutyrylmorphine-6-O-sulfate Zwitterion

The procedure employed was similar to the one utilized for obtaining the 6-O-sulfate ester of 3-O-acetylmorphine. This procedure afforded 80 mg (34.4%) of the colorless solid product from 190 mg (0.54 mmol.) of 3-O isobutyrylmorphine. TLC (Chloroform: Methanol: Water (2:1:0.5), $R_f$=0.4), m.p.: 265–270° C. (dec.), MS(pos-FAB) m/z 436 (M+H)+. Elemental analysis; Calcd. for $C_{21}H_{25}NO7S$. V3H20: C, 57.13; h, 5.85; N, 3.17; s, 7.26. Found; C, 57.34; H, 5.75; N, 3.19; s, 7.24.

3-O-Pivaloylmorphine-6-O-sulfate Zwitterion

The procedure employed was similar to the one used for obtaining the 6-O-sulfate ester of 3-O-acetylmorphine. This procedure afforded 132 mg (54.4%) of the golden brown solid product from 200 mg (0.54 moles) of 3-Opivaloylmorphine m.: 245–250° C. (dec), MS (neg-FAB) m/z 448 (M−H). Elemental analysis: Calcd. for $C_{22}H_{27}NO7S$.1/2H2O: C, 57.63; H, 6.15; N, 3.05; s, 6.99. Found: C, 57.74; H, 6.31; N. 2.98; S, 7.05.

3-O-Benzoyl-7,8-dihydromorohine-6-O-sulfate Zwitterion

The procedure employed was similar to the one used for obtaining the 6-O-sulfate ester of 3-O-acetyl-morphine. This procedure afforded 190.5 mg (79.1%) of the colorless solid product from 200 mg (0.51 mmole) of 3-O-benzoyl-7,8-dihydromorphine TLC [Propanol: Chloroform: Methanol:Water(2:2:1:0.4), Rf=0.31 m.p.: 280–285° C. tdec.), MS(neg-FAB) m/z 470 (MH). Elemental analysis: Calcd. for $C_{24}H_{25}NO_7s.2H_2O$: C, 56.79; H, 5.76; N, 2.76. Found: C, 56.99; H, 5.51; N, 2.70.

3-O-Acetyl-N-methylmorphinium-6-O-sulfate Inner Salt

The procedure employed was similar to the one used for obtaining the 6-O-sulfate ester of 3-O-acetyl-morphine. This procedure afforded 43 mg (47.8%) of the colorless solid product from 100 mg (0.21 mmol) of the 3-O-Acetyl-N-methylmorphinium iodide salt. TLC [Propanol: Chloroform: Methanol: Water (2:2:1:0.4), Rf=0.1]. m.p: 260–265° C. (dec.) MS (neg-FAB) mlz 420 (M−H). Elemental analysis: Calcd. for $C_{20}H_{23}NO7S$ 1/2H2O: C, 54.67; H, 5.50; N,3.19; S, 7.30. Found (C, 54.67; H, 5.79; N, 3.37; S, 7.72.

3-O-Benzoyl-N-methylmorphinium-6-O-sulfate Zwitterion Inner Salt

The procedure employed was similar to the one utilized for obtaining the 6-O-sulfate ester of 3-O-acetylmorphine. This procedure afforded 12.1 mg (33.3%) of the colorless solid product from 40 mg (0.08 mmol) of the 3-O-benzoyl-N-methylmorphinium iodide. TLC [Propanol: Chloroform: methanol: Water (2:2:1:0.4), Rf=0.1] m.p: 245–250° C. (dec.) MS (neg-FAB) m/z 482 (M−H).

Morphine-6-O-Sulfate

3-O-Acetylmorphine-6-O-sulfate zwitterion (200 ma, 0.49 mmol) was dissolved in 5% methanolic sodium hydroxide solution (20 ml). The reaction mixture was stirred at ambient temperature for one hour. The resultant solution was then concentrated to approximately one third of its original volume by rotary evaporation under reduced pressure at 40° C. To this concentrated solution was added dropwise, with stirring, a 10% solution of acetic acid (7 ml) until the pH of the solution was 6. The reaction mixture was then placed in the refrigerator for two hours, during which time colorless needle shaped crystals of the product were formed. Subsequent filtration and washing with water afforded 147.4 mg (82.2%) of morphine 6-O-sulfate. m.p.: 270–275° C. (dec.) MS (neg-FAB) mJz 364 (M−H). Elemental analysis: Calcd. for $C_{17}HlgNO6S$ 2/3H2O: C, 54.97; H. 5.14; N, 3.77; S, 8.63. Found: C, 54.92; H, 5.35; N, 3.75; S, 8.54.

SCHEMES FOR PREPARING COMPOUNDS OF THE INVENTION

Synthesis schemes for preparing the compounds of the invention are set forth in Schemes 1 and 2 below.

Scheme 1

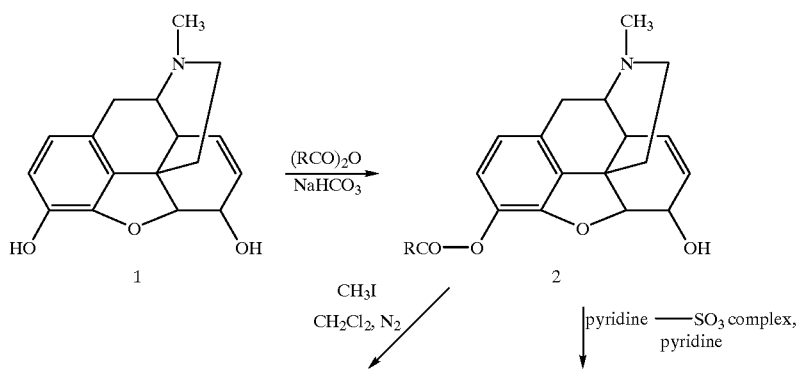

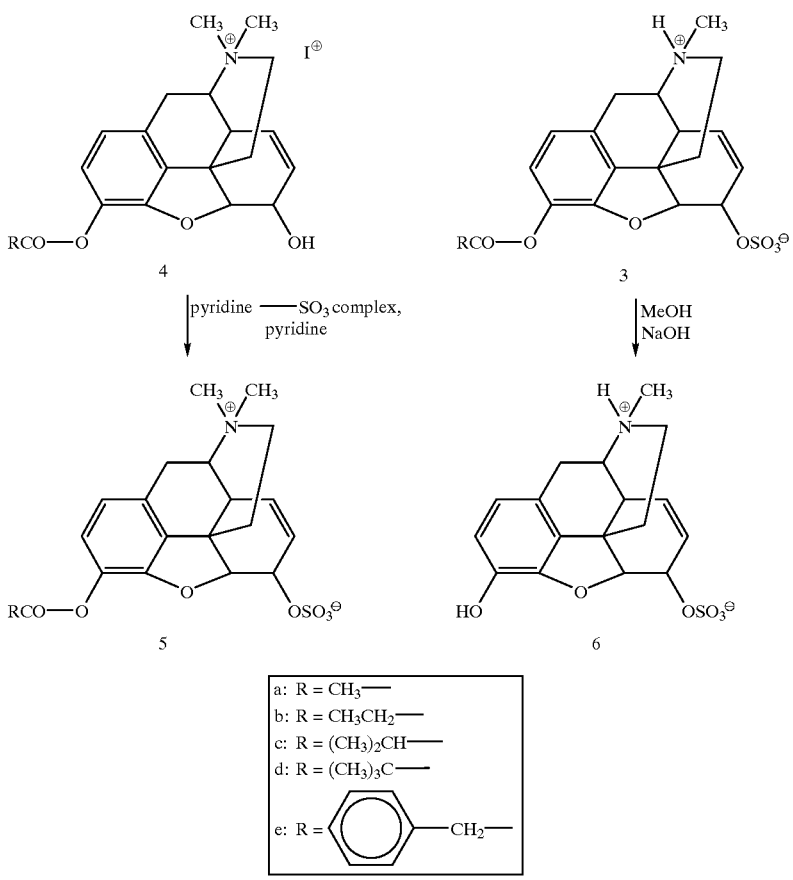
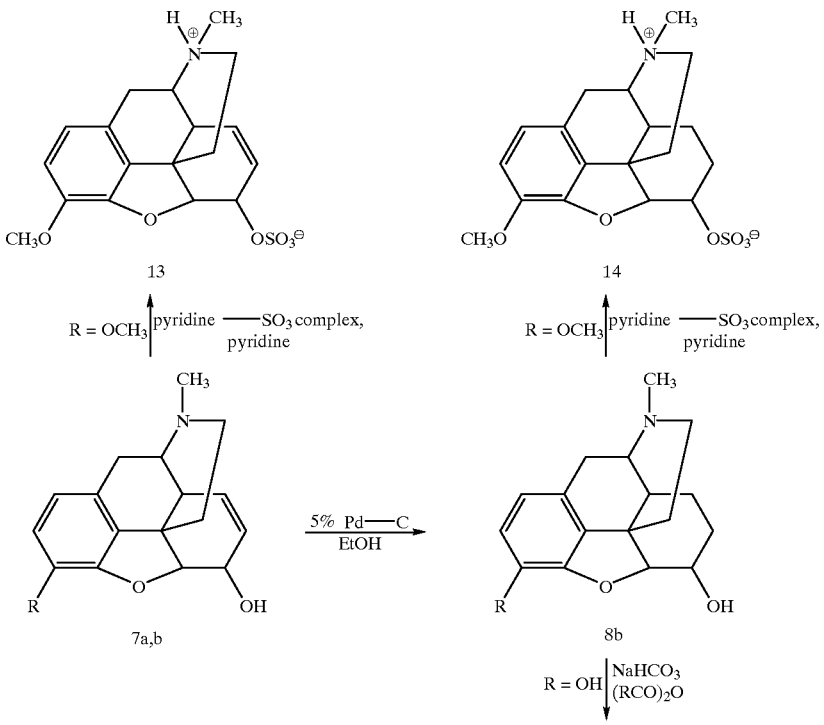

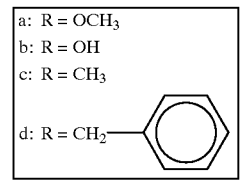
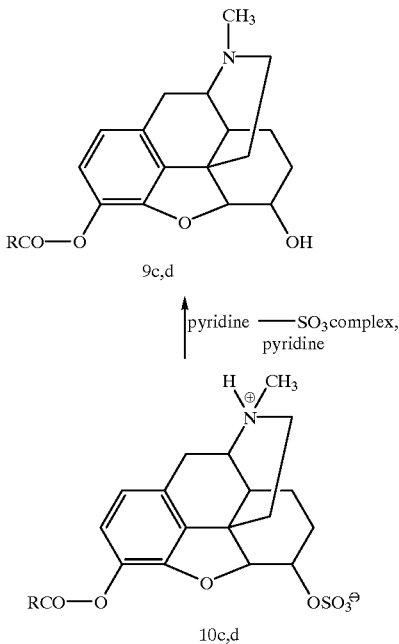

Statistical Analysis

The data are presented as mean±S.E.M. for the given number of rats. Two-way repeated measure with interaction ANOVA followed by Tukey's post hoc test for comparisons was utilized for analysis between groups treated with different drugs and tested for analgesia.

Figure 2:
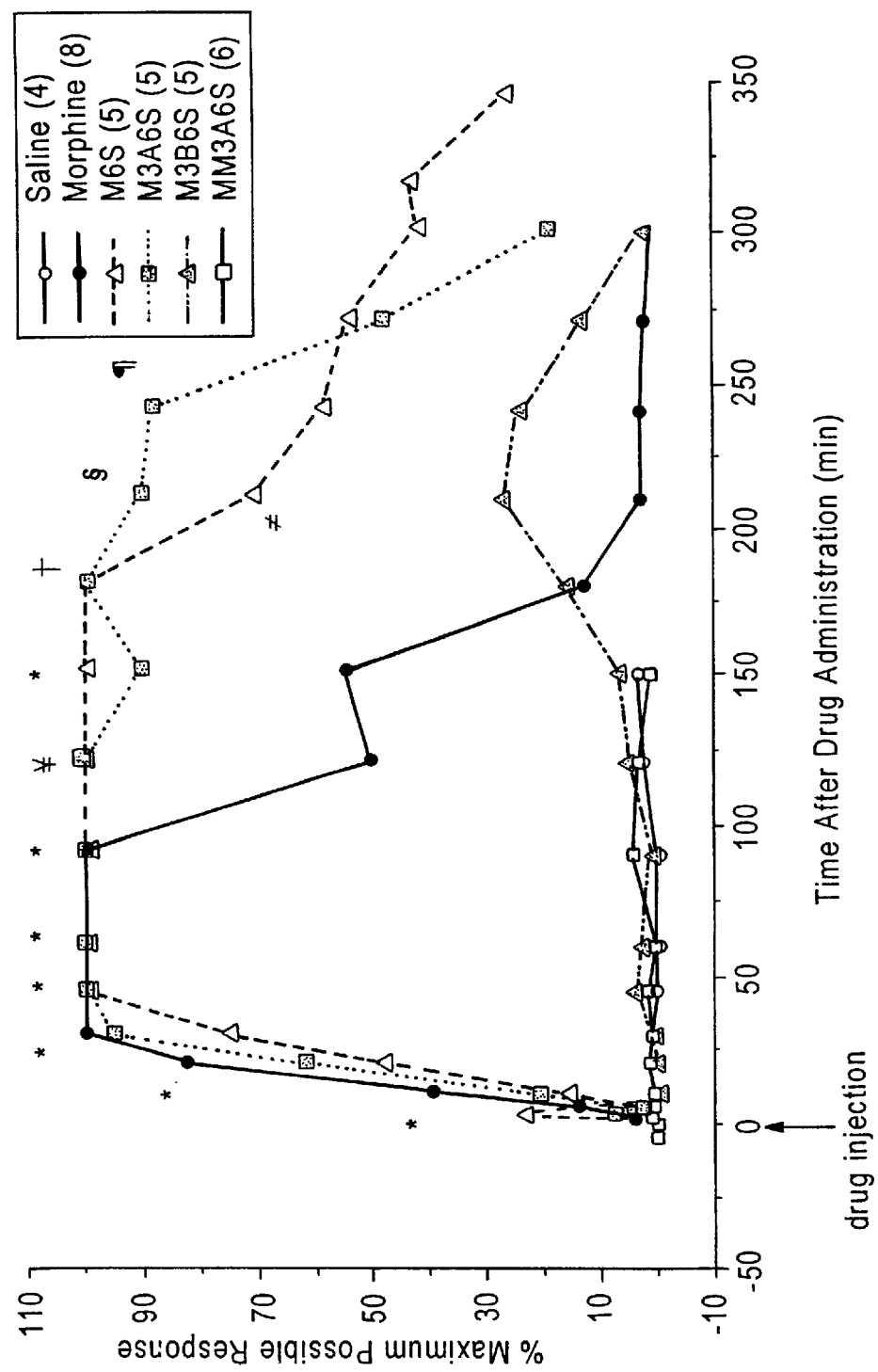
FIG. 2 shows antinociceptive response to subcutaneous treatment with morphine. Antinociception is shown as the percent of maximum possible response in the tail-flick test. Free base morphine was used for subcutaneous administration (5 mg/kg, 0.0175 mmole) Equimolar doses of morphine derivatives were as follows: M6S (6.4 mg/kg); M3A6S (7.1 mg/kg); M3B6S (8.2 mg/kg); and MM3A6S (7.4 mg/kg) were administered subcutaneously. Predrug response latencies for saline, morphine, M6S, M3A6S, M3B6S, and MM3A6S were 2.15, 1.96, 2.37, 1.79, 1.95 and 2.11 seconds respectively.

Antinociceptive Activity of Morphine-6-O-Sulfate yDerivatives After Subcutaneous Injection The antinociceptive activities of M6S, M3A6S, M3B6S, MM3A6S, and morphine, as determined by the tail-flick method following subcutaneous injection, are illustrated in FIG. 2. The onset of morphine (5 mg/kg, sc) analgesia started within 10 minutes of administration; maximal analgesic response was achieved within 30 minutes and was maintained for 60–80 minutes. This analgesic profile for morphine is similar to other published reports [5,8]. An equimolar dose of M6S produced a maximal analgesic effect similar to morphine within 30 minutes after administration. However, the maximal analgesic effect lasted over 3 hours. An equimolar dose of M3A6S produced an analgesic profile similar to that of M6S with respect to onset of action and maximal analgesic effect, which was maintained for 4 hours. Interestingly, M3B6S at an equimolar dose, showed only a gradual onset of weak analgesia over 100 minutes, which reached a maximum equivalent to only 27% of maximal analgesia over 4 hours. The dipolar betaine, MM3A6S, was devoid of any analgesic properties when tested at an equivalent molar dose.

Figure 3:
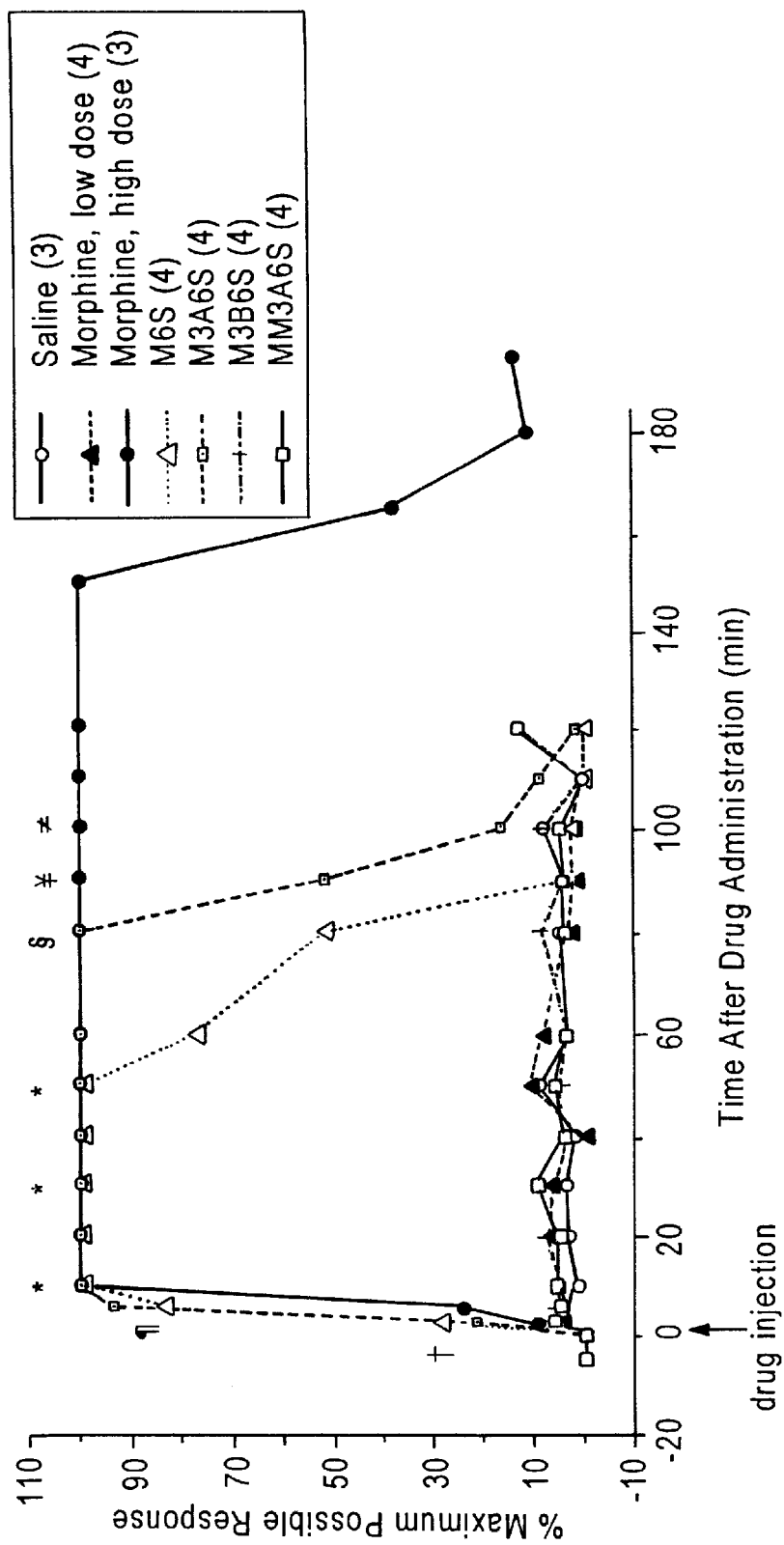
FIG. 3 shows antinociceptive response to treatment with saline vehicle, morphine and morphine derivatives. For intracerebroventricular drug administration, 2 doses of morphine were used; low dose morphine (0.236 µg/rat, 0.83 pmole µmole/rat as free base) and high dose of morphine (23.6 µg/rat, 83 pmole/rat). Doses of morphine derivatives administered intracerebroventricularly were equimolar to the low dose of morphine and were as follows: M6S (0.22 µg/kg); M3A6S (0.25 µg/kg); M3B6S (0.29 µg/kg); and MM3A6S (0.26 µg/kg). Antinociception is shown as the percent of maximum possible response in the tail-flick test. Predrug response latencies for saline, morphine low dose, morphine high dose, M6S, M3A6S, M3B6S, and MM3A6S were 2.05, 2.06, 1.69, 1.92, 2.62, 2.06 and 1.82 seconds respectively.

Antinociceptive Activity of Morphine-6-O-Sulfate Derivatives After Intracerebroventricular Administration The above compounds were also evaluated for analgesic activity by the tail-flick assay after administration by intracerebroventricular injection. These results are shown in FIG. 3. Two doses of morphine were initially employed. The lower dose of morphine (0.23 µg/4 µl/rat) failed to produce an analgesic effect. The higher dose (23.6 µg/4 µl/rat) produced a rapid analgesic response (6 minutes after icv injection), and maximal analgesia was achieved within 10 minutes of administration and maintained for an additional 3 hours. Administration of M6S at a molar dose equivalent to the lower dose of morphine produced a maximal analgesic effect, within 10 minutes, that was maintained for 70 minutes. M3A6S administered at an equivalent molar dose to M6S exhibited a similar profile, maximal analgesia being established at 10 minutes and lasting for an additional 90 minutes. A similar dose of either M3B6A or MM3A6S afforded no analgesic response over the 100 minute time period examined.

Figure 4:
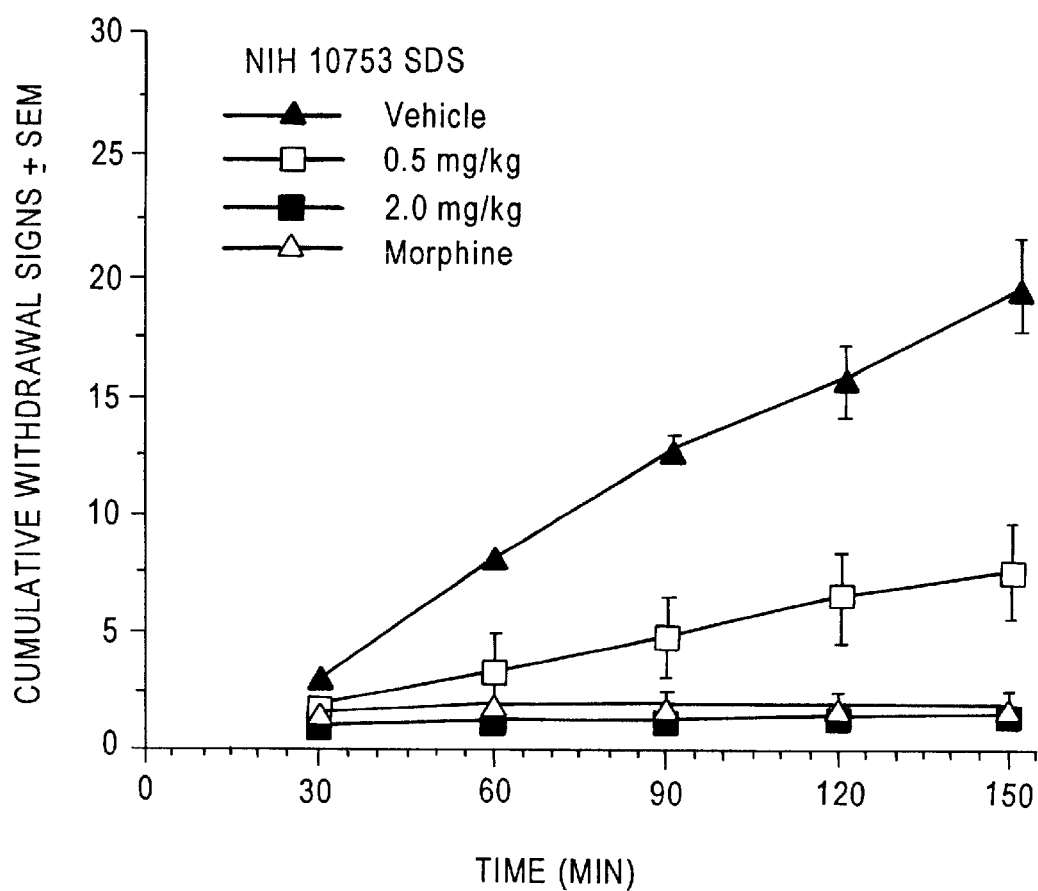
FIG. 4 shows precipitated morphine withdrawal with time after the administration of morphine in the Rhesus monkey. Precipitated withdrawal test initiated by injection of morphine control 2.5 hrs after an injection and animals observed for signs of withdrawal. Time on the abscissa represents time after administration of morphine control. On the ordinate is the cumulative withdrawal signs which are composed of unit scores given that record the manifestation of characteristic withdrawal symptoms. Injection vehicle: saline.
Figure 5:
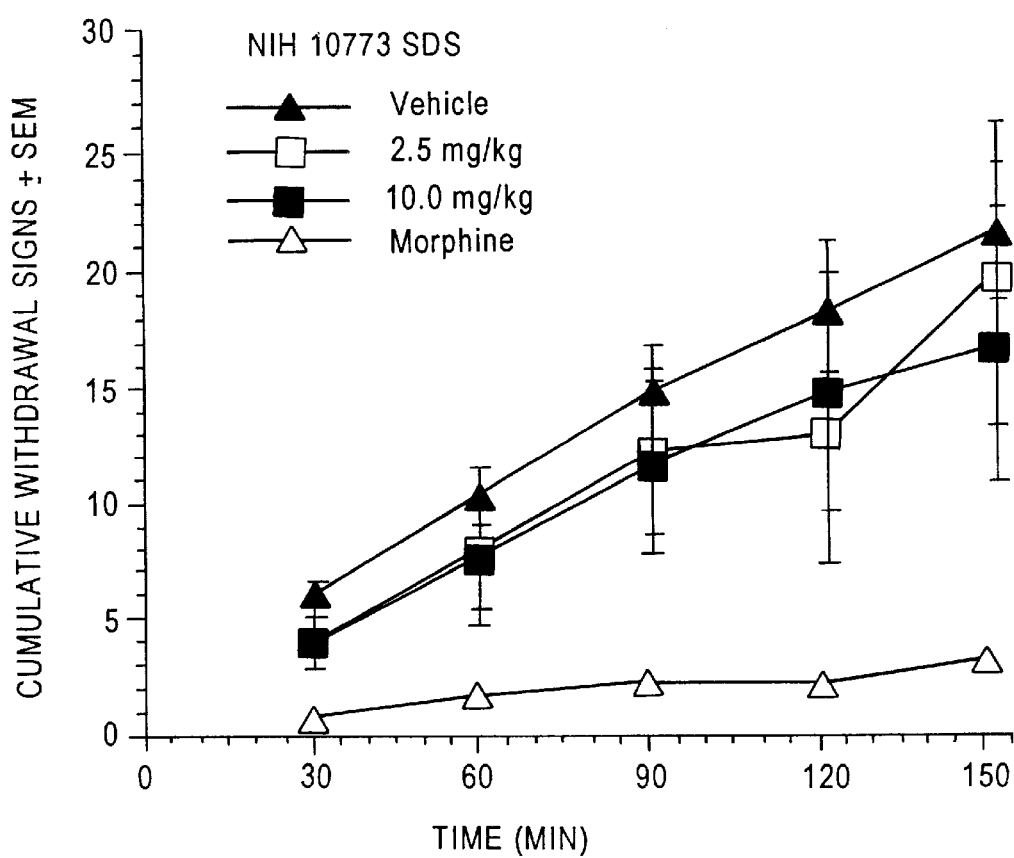
FIG. 5 shows precipitated morphine withdrawal with time after the administration of M3A6S in the Rhesus monkey. Precipitated withdrawal test initiated by the injection of M3A6S 2.5 hrs after an injection of morphine and animal observed for signs of withdrawal. All experimental conditions are similar to that in FIG. 4 except that the injection vehicle is 25% Tween in water with gentle warming.
Figure 6:
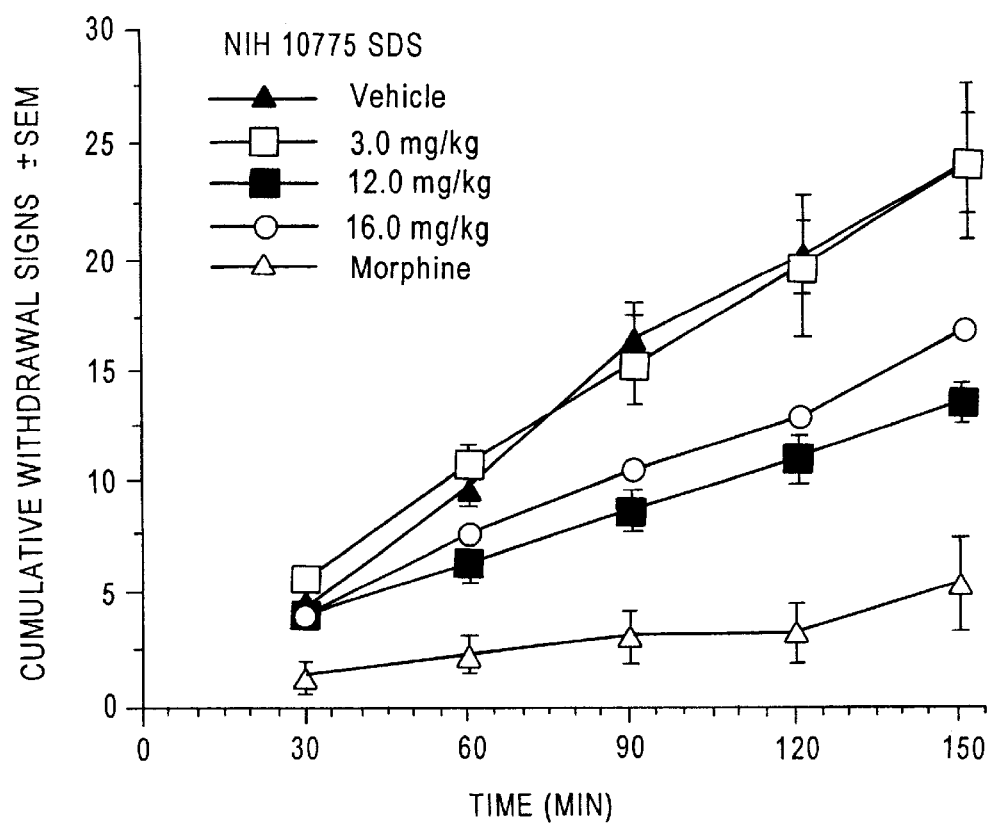
FIG. 6 shows precipitated morphine withdrawal with time after the administration of DM3A6S in the Rhesus monkey. Precipitated withdrawal test initiated by the injection of DM3A6S 2.5 hrs after an injection of morphine and animal observed for signs of withdrawal. All experimental conditions are similar to that in FIG. 4.
Figure 7:
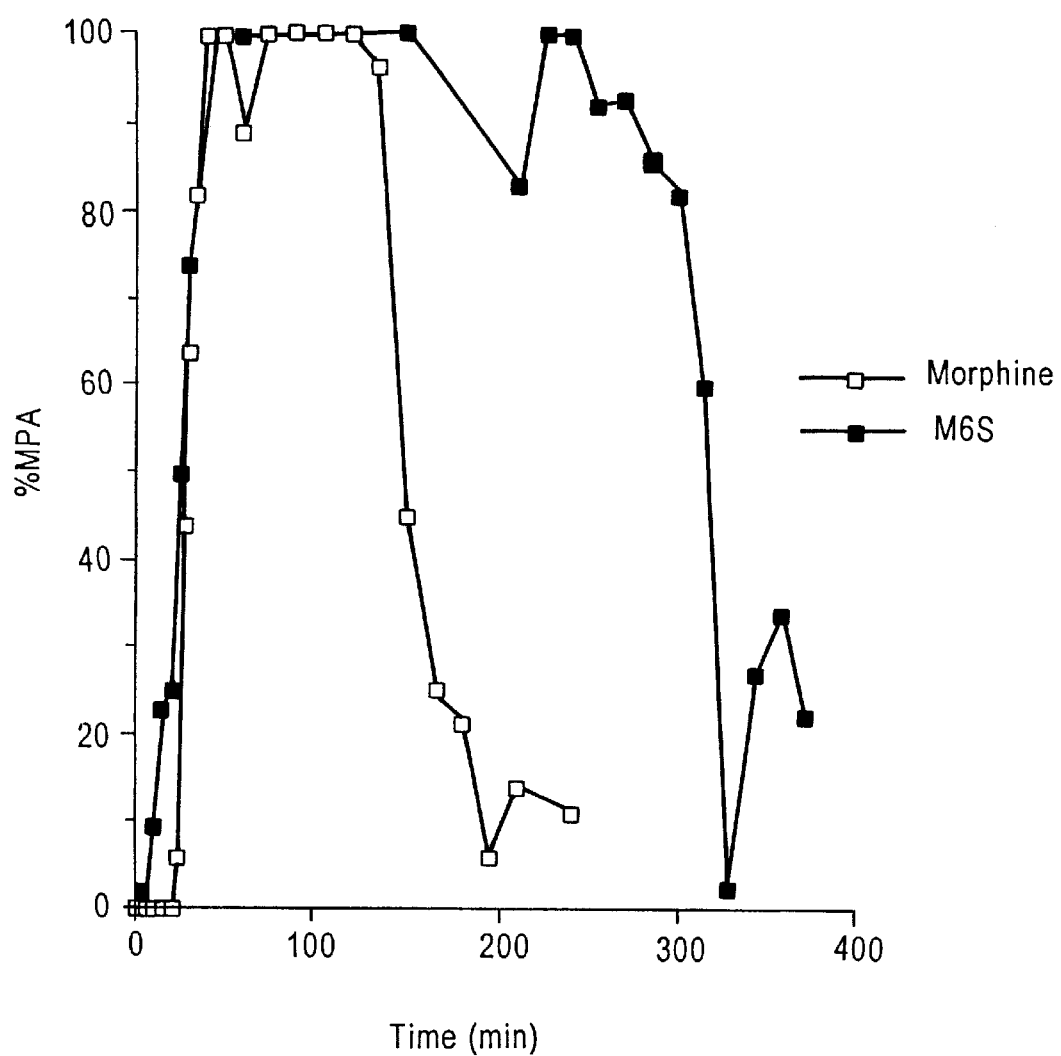
FIG. 7 shows the analgesic profile of M6S. Effect of morphine 6-O-sulfate (M6S) in comparison to morphine on nociception after subcutaneous (s.c.) administration in the rat tail flick (RTF) assay. Dose of morphine and M6S administered: 0.0175 mmol/kg wt. of animal/ml. Injection vehicle: sesame seed oil, n=5. Time on the abscissa represents time relative to morphine administration. Antinociception is shown as the percent of maximum possible analgesia (%MPA). Pre-drug response latencies (basal analgesia) for morphine and M6S were 2.01 and 2.23, respectively.
Figure 8:
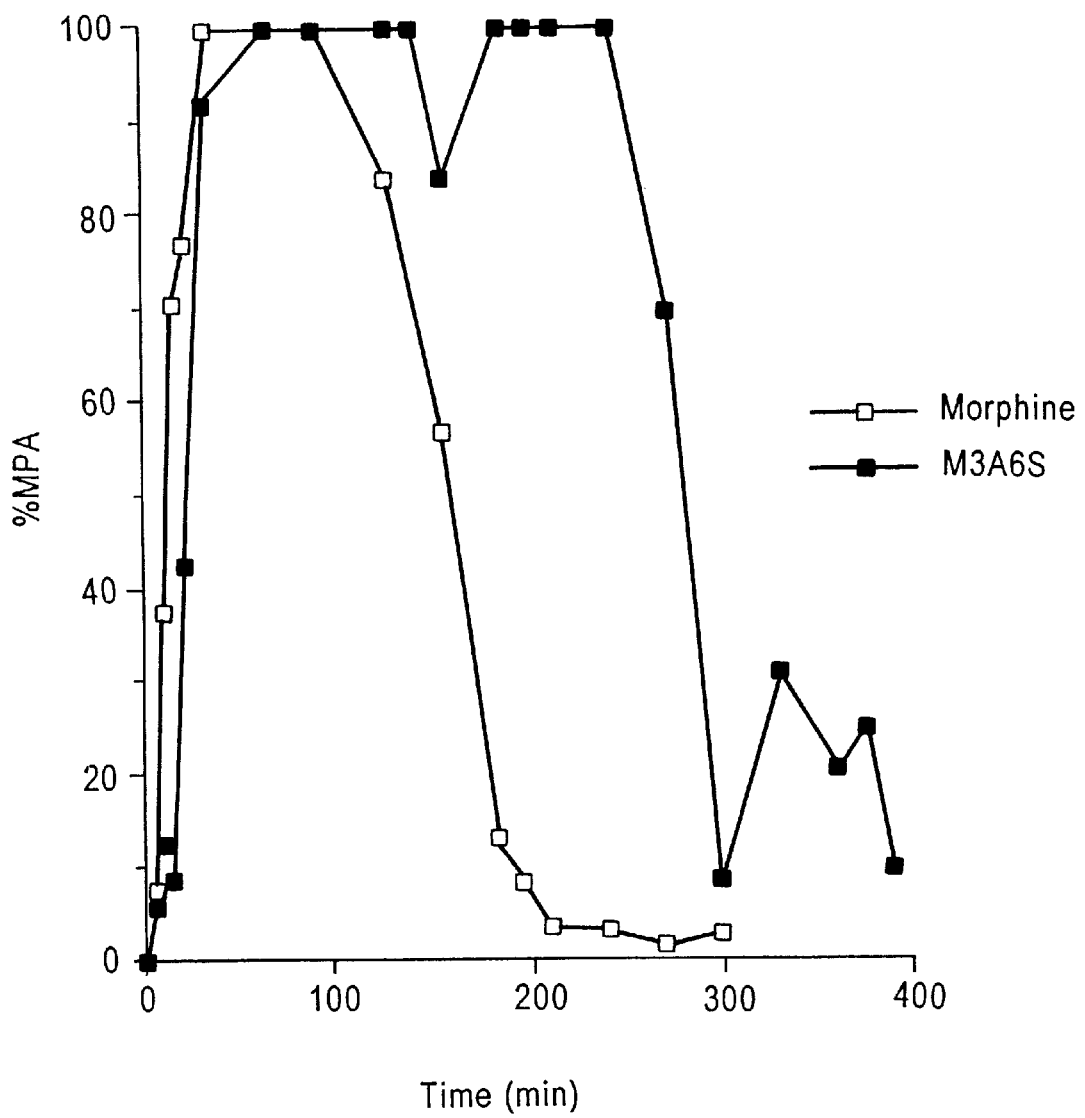
FIG. 8 shows the analgesic profile of M3A6S. Effect of 3-O-acetylmorphine-6-O-sulfate (M3A6S), in comparison to morphine, on nociception after s.c. administration in the RTF assay. All experimental details remain the same (as described in FIG. 7) except that for M3A6S, n=4 and the basal analgesia value is 1.77.
Figure 9:
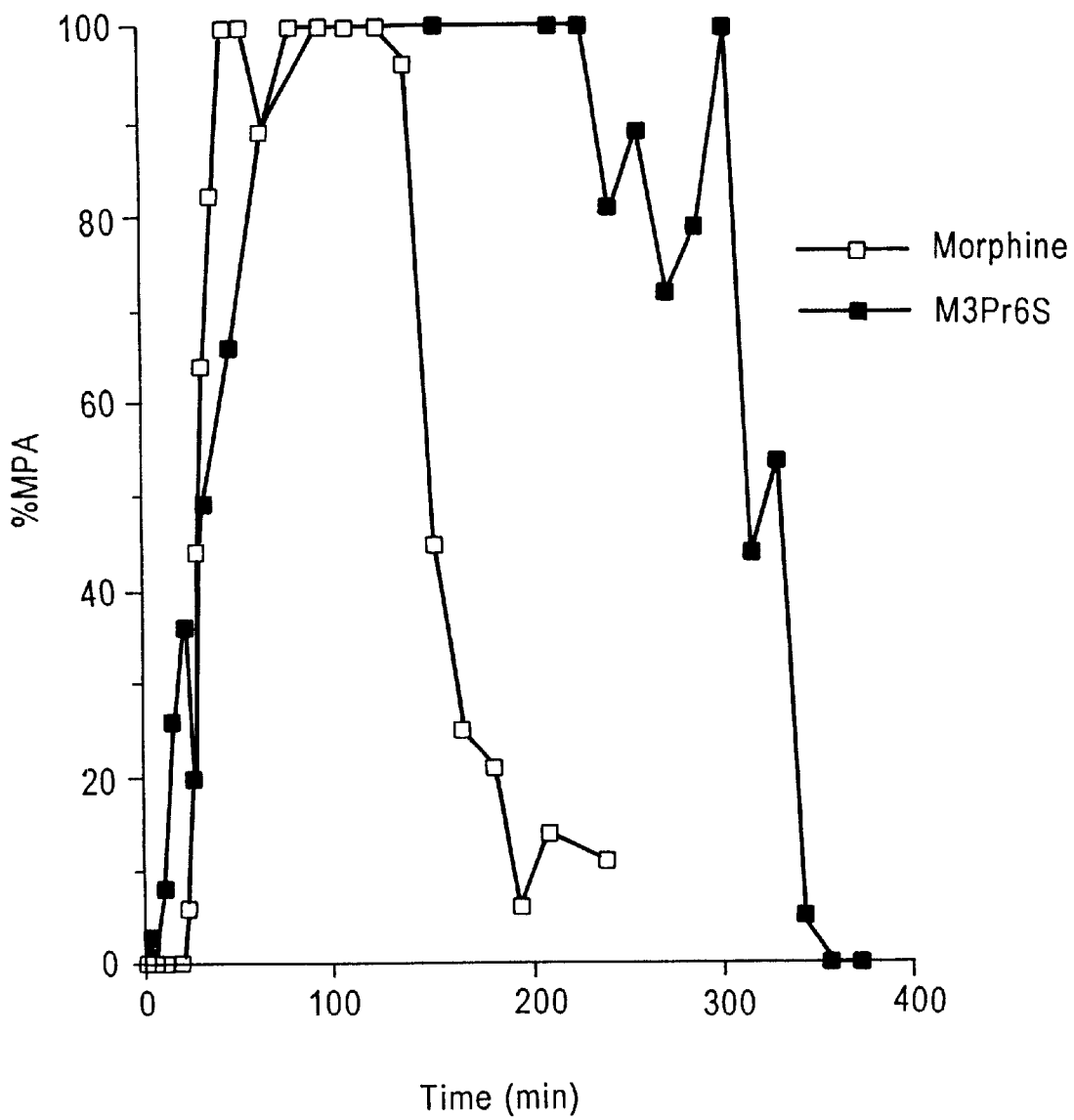
FIG. 9 shows the analgesic profile of M3Pr6S. Effect of 3-O-propionylmorphine-6-O-sulfate (M3Pr6S), in comparison to morphine, on nociception after s.c. administration in the RTF assay. All experimental details remain the same (as described in FIG. 7) except that for M3Pr6S, n=3 and the basal analgesia value is 1.97.
Figure 10:
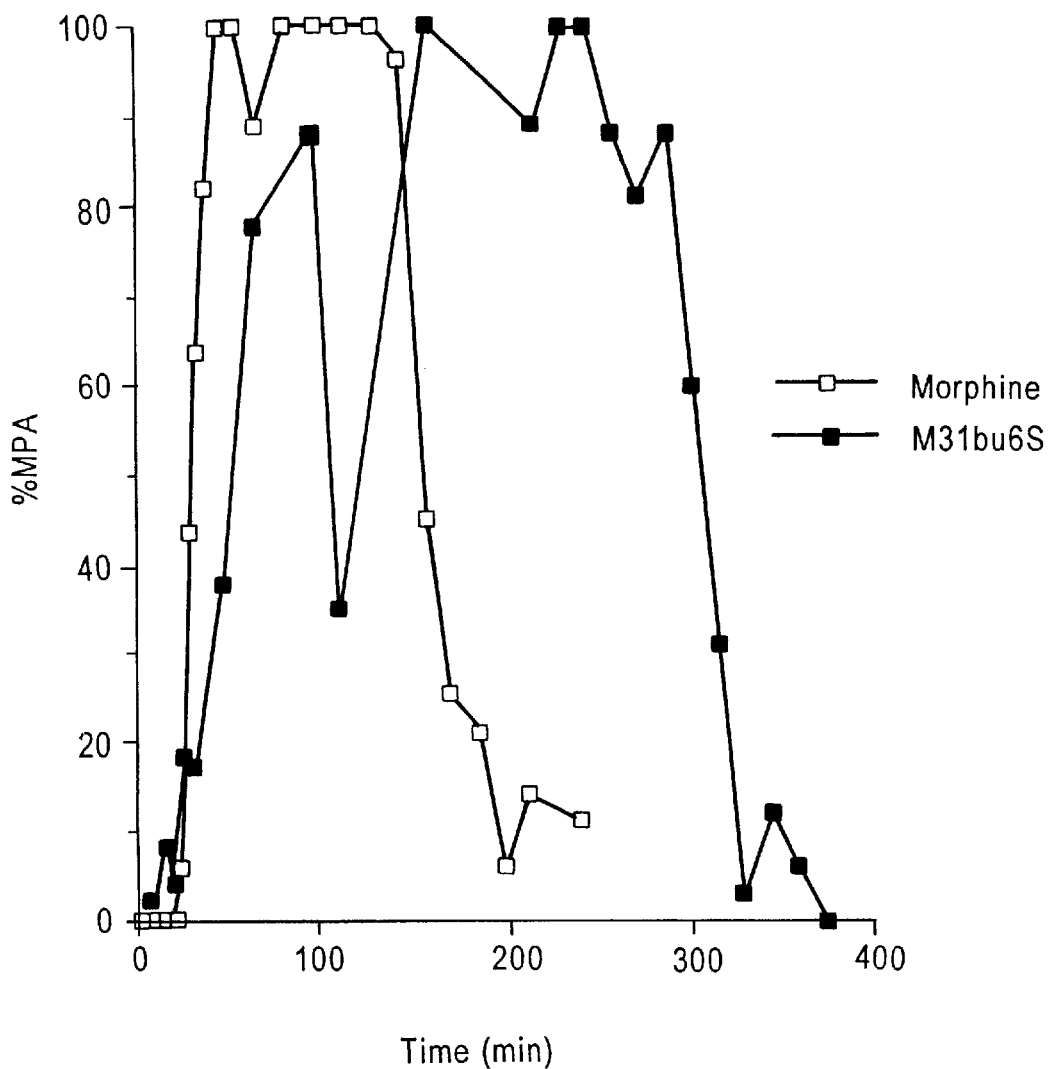
FIG. 10 shows the analgesic profile of M3Ibu6S Effect of 3-O-isobutyrylmorphine-6-O-sulfate (M3Ibu6S), in comparison to morphine, on nociception after s.c. administration in the RTF assay. All experimental details remain the same (as described in FIG. 7) except that for M3Ibu6S, n=4 and the basal analgesia value is 1.86.
Figure 11:
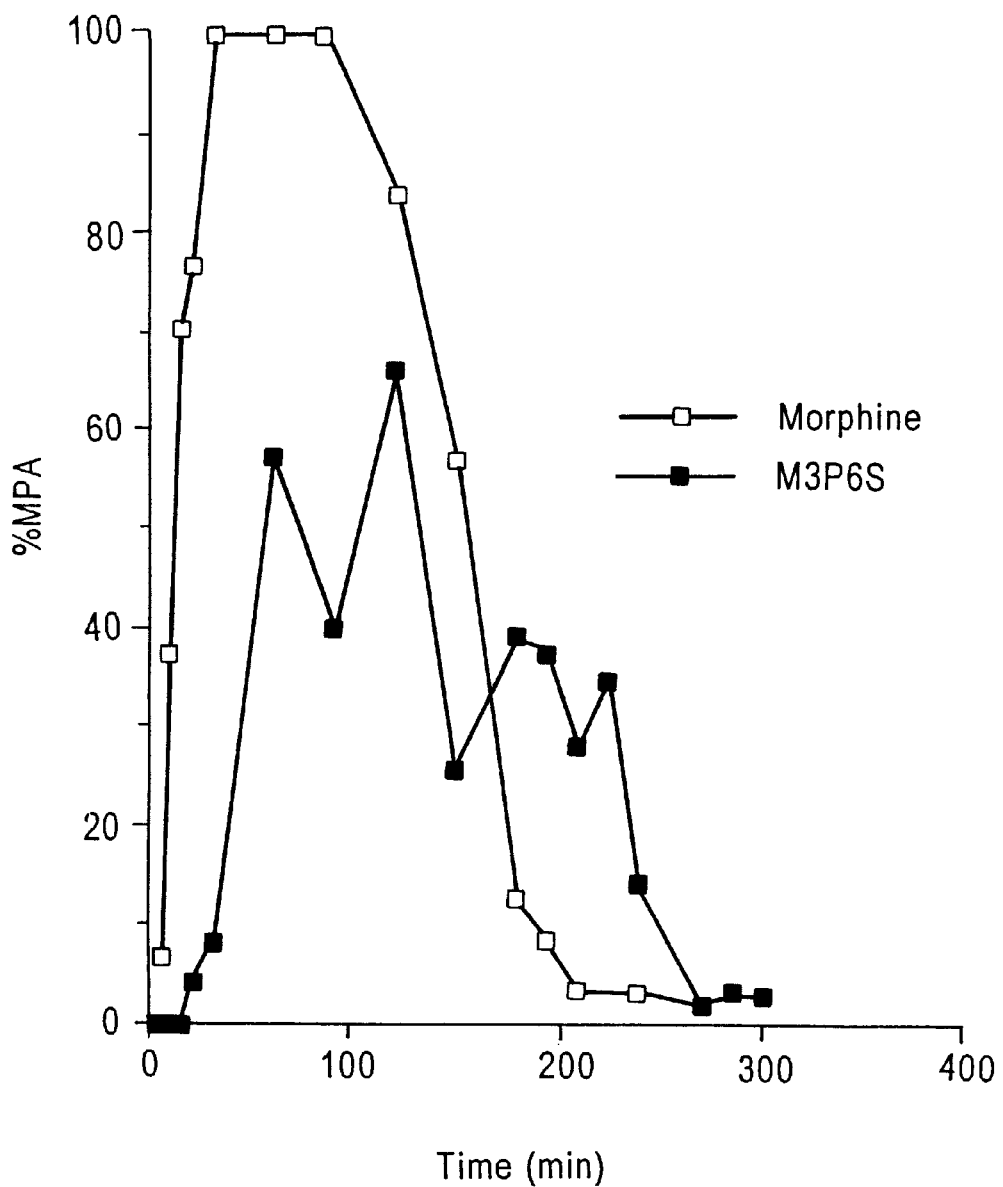
FIG. 11 shows analgesic profile of M3P6S Effect of 3-O-pivaloylmorphine-6-O-sulfate (M3P6S), in comparison to morphine, on nociception after s.c. administration in the RTF assay. All experimental details remain the same (as described in FIG. 7) except that for M3P6S, n=6 and the basal analgesia value is 1.95.
Figure 12:
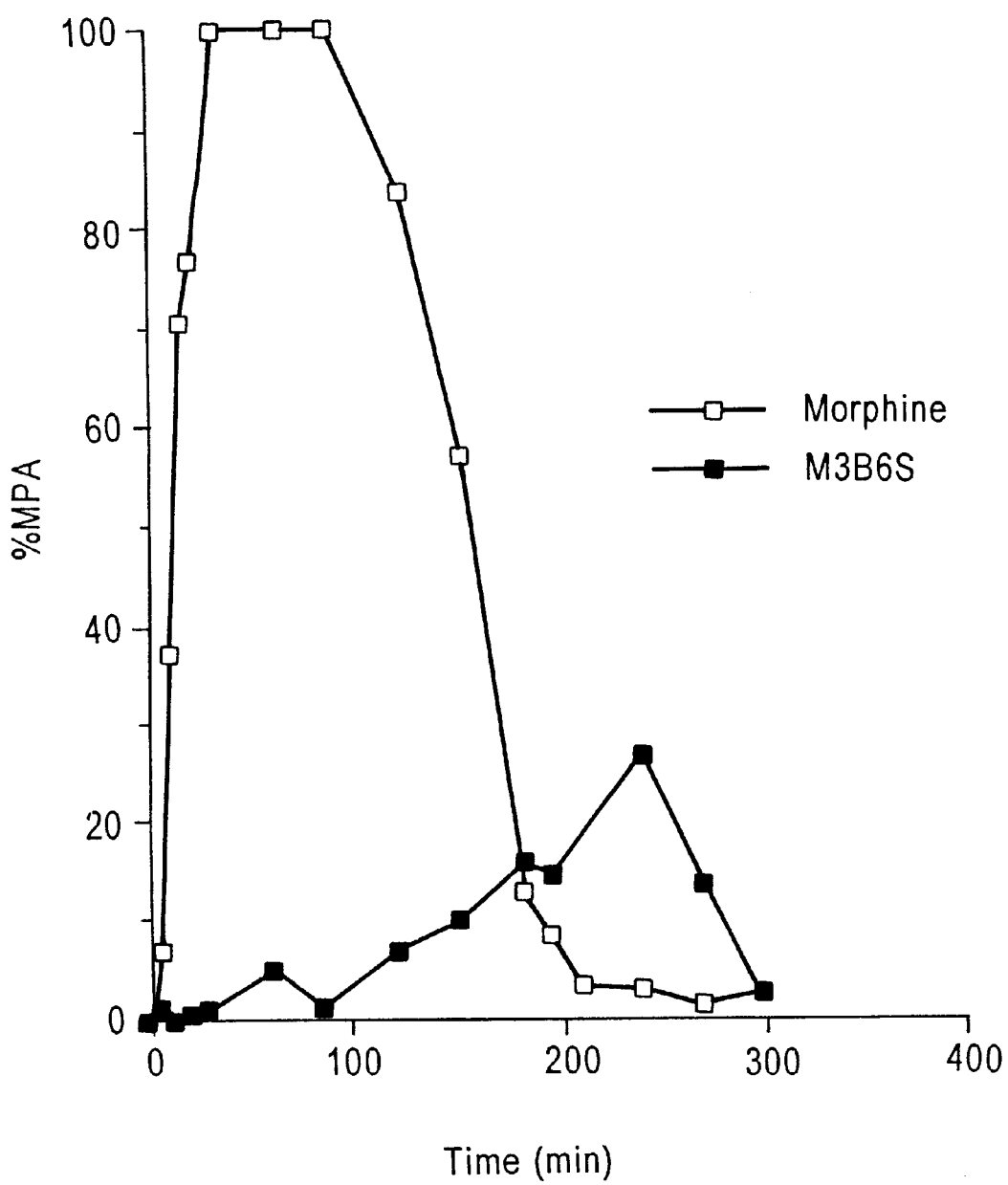
FIG. 12 shows analgesic profile of M3B6S Effect of 3-O-benzoylmorphine-6-O-sulfate (M3B6S), in comparison to morphine, on nociception after s.c. administration in the RTF assay. All experimental details remain the same (as described in FIG. 7 except that for M3B6S, n=3 and the basal analgesia value is 1.91.
Figure 13:
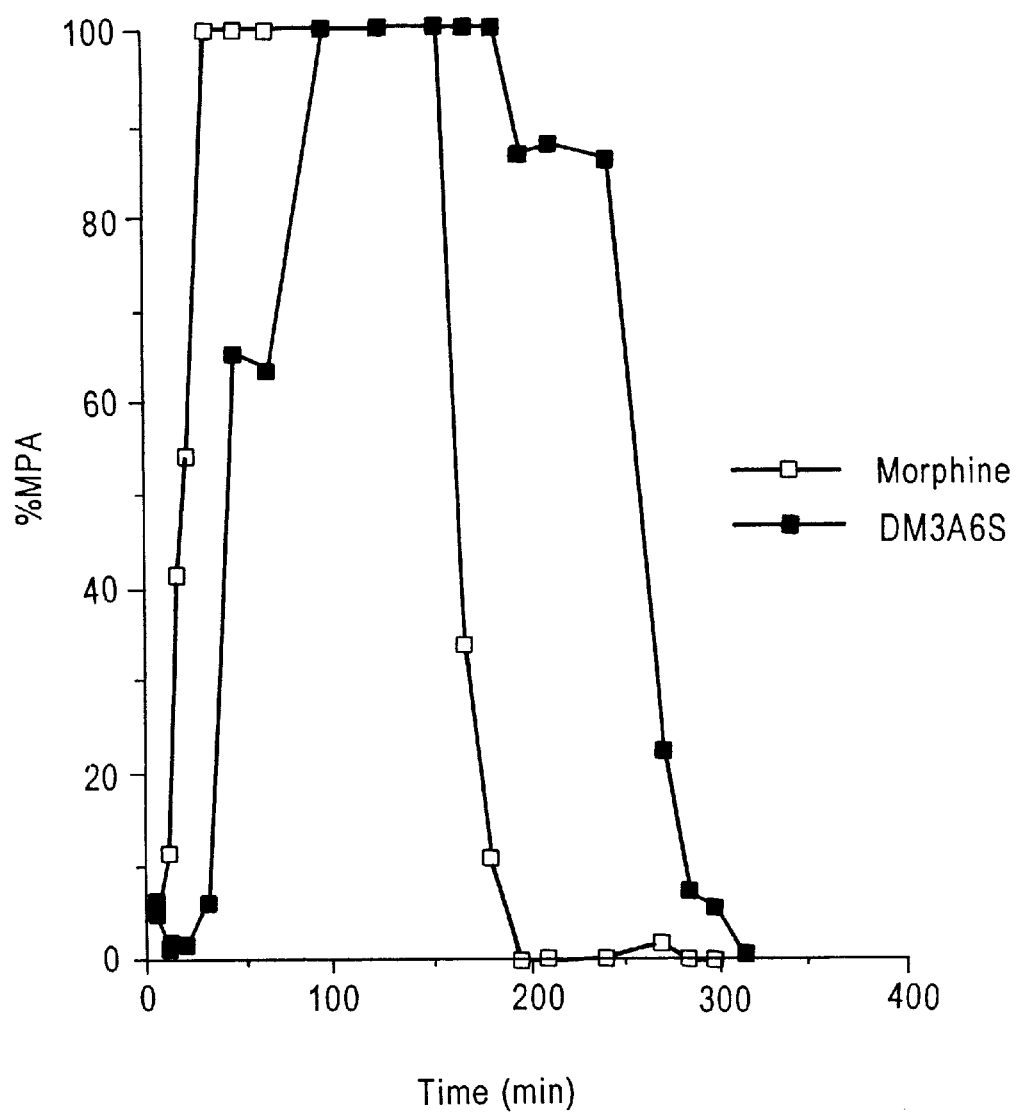
FIG. 13 shows analgesic profile of DM3A6S Effect of 3-O-acetyl-7,8-dihydromorphine-6-O-sulfate (DM3A6S), in comparison to morphine, on nociception after s.c. administration in the RTF assay. All experimental details remain the same (as described in FIG. 7) except that for DM3A6S, n=3 and the basal analgesia value is 1.90.
Figure 14:
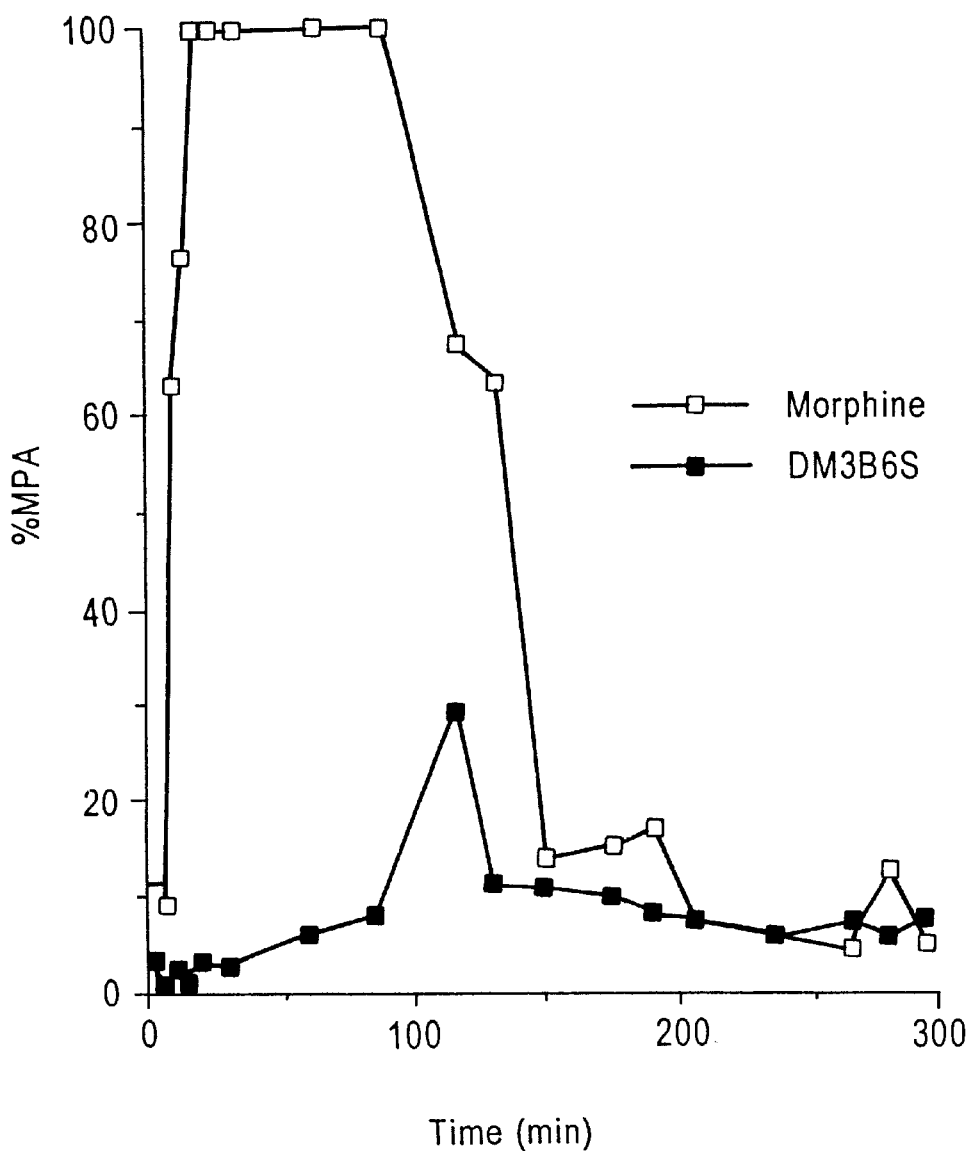
FIG. 14 shows analgesic profile of DM3B6S Effect of 3-O-benzoyl-7,8-dihydromorphine-6-O-sulfate (DM3B6S), in comparison to morphine, on nociception after s.c. administration in the RTF assay. All experimental details remain the same (as described in FIG. 7) except that for DM3B6S, n=4 and the basal analgesia value is 1.78.
Figure 15:
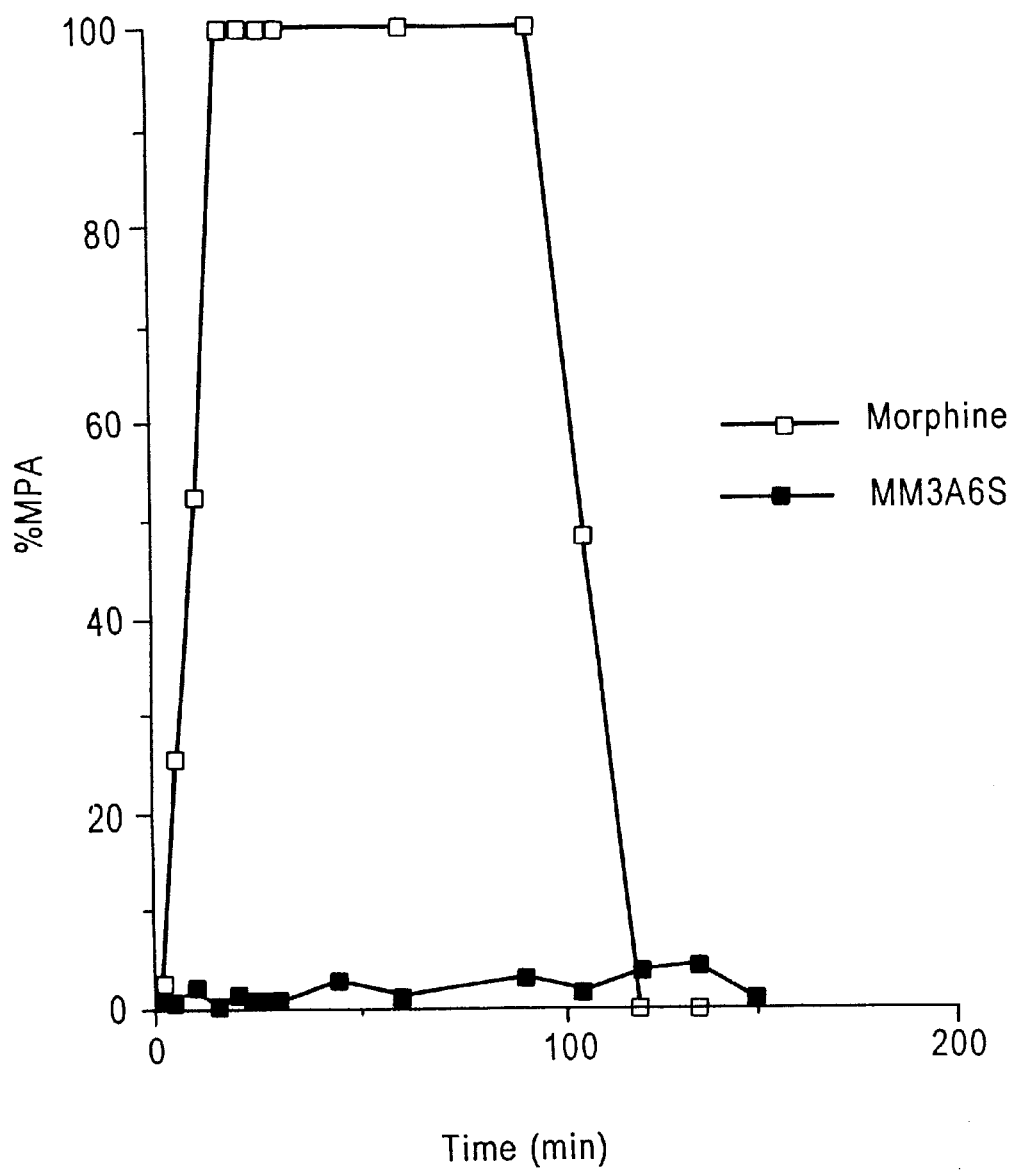
FIG. 15 shows analgesic profile of MM3A6S., Effect of 3-O-acetyl-N-methylmorphinium-6-O-sulfate (MM3A6S), in comparison to morphine, on nociception after s.c. administration in the RTF assay. All experimental details remain the same (as described in FIG. 7) except that for MM3A6S, n=5 and the basal analgesia value is 2.03.
Figure 16:
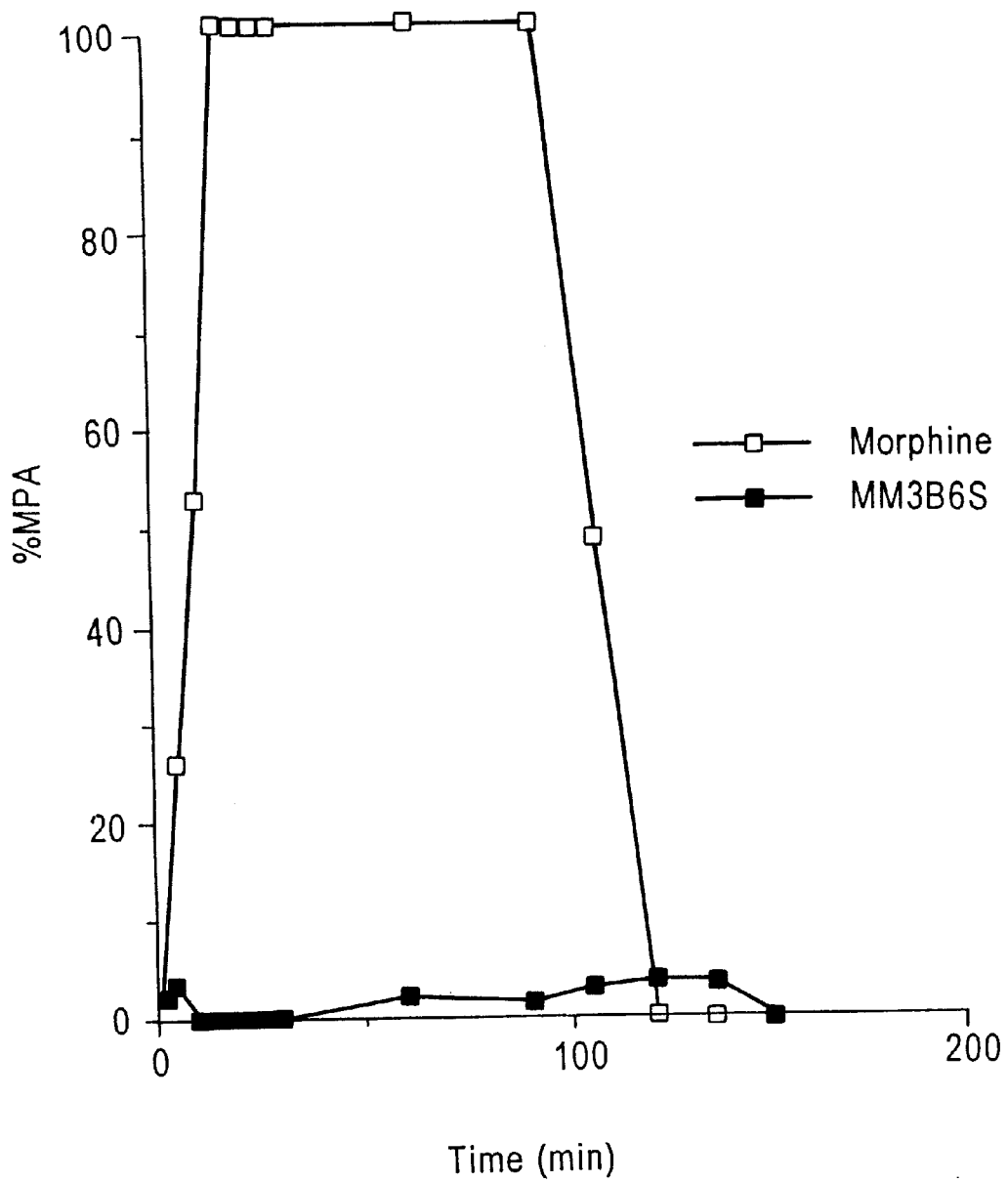
FIG. 16 shows analgesic profile of MM3B6S. Effect of 3-O-benzoyl-N-methylmorphinium-6-O-sulfate (MM3B6S), in comparison to morphine, on nociception after s.c. administration in the RTF assay. All experimental details remain the same (as described in FIG. 7) except that for MM3B6S, n=4 and the basal analgesia value is 2.23.

Single Dose Substitution and Precipitated Morphine Withdrawal Studies of M3A6S and DM3A6S in Morphine Dependent Rhesus Monkeys The precipitated morphine withdrawal test was carried out on the two test compounds, M3A6S and DM3A6S and on morphine sulfate salt for comparison. The test was initiated by the injection of the drug 2½ hours after an injection of morphine, and animals were observed for signs of withdrawal. The single dose substitution test was started approximately 15 hours after the last dose of morphine, at which time the animals were showing withdrawal signs. The onset and duration of action of the test drugs were noted. In both tests, vehicle control and an appropriate positive control (morphine sulfate, 3.0 mg/kg) along with 2 or 3 doses of the test compound were randomly allocated to 4 or 5 monkeys of a group. Both drugs were given subcutaneously (1 ml/kg). The observer was "blind" with regard to the treatment given. FIGS. 4, 5 and 6 illustrate the cumulative withdrawal sign scores given with time after the administration of morphine sulfate salt, M3A6S, and DM3A6S, respectively. The cumulative withdrawal signs are composed of unit scores given, that record the manifestation of characteristic withdrawal symptoms. These symptoms include the animals lying on their side or their abdomen, drowsiness, fighting, avoiding contact, crawling and rolling, restlessness (pacing), posis, tremors, retching, vomiting, coughing, vocalizing when abdomen palpitated, a rigid abdomen and salivation.

The sulfate salt of morphine was examined as a positive control for similar tests on the compound M3A6S and DM3A6S (FIGS. 5 & 6). FIG. 5 displays the withdrawal profile for the test compound M3A6S (NIH 10773). As is clearly seen, M3A6S at the doses 2.5 and 10.0 mg/kg did not substitute for morphine, nor did it exacerbate withdrawal during the observed time frame of 2½ hours. The drug vehicle in this case was 10–15% DMSO in water. To distinguish true effects from artifacts, the profile upon administration of the vehicle is also displayed. The monkey data therefore suggests the absence of any $\mu$-like activity for the compound M3A6S. The compound DM3A6S also displays a profile similar to M3A6S. As seen from FIG. 6, at the doses 3.0, 12.0 and 16.0 mg/kg. DM3A6S showed an overall inconsistent dose response attenuation of withdrawal signs. It did not substitute for morphine nor did it exacerbate withdrawal. Again, this data suggests the absence of any $\mu$-like activity for the compound DM3A6S. However, it is known that certain selective kappa agonists have profiles of activity similar to that of M3A6S and DM3A6S.

Specific Transport

Solubility in lipid is not the sole determinant of the rate of entry into brain of a compound. If this were so, the brain would be deprived of adequate amounts of several metabolic substrates on which it depends. In particular, the partition coefficient of glucose is so low that unfacilitated diffusion would be quite inadequate to supply the amounts of this compound required for cellular respiration. Crone (1965) and others (Gjedde, 1984, 1980 and Pardridge, 1983) have demonstrated the specific transport of glucose at the blood brain barrier. Oldendorf's intracarotid tissue sampling technique (1970) for characterizing specific transport at the endothelium, has led to the recognition of specific mechanisms facilitating the transport of certain compounds within several groups: i.e., monosaccharides (D-glucose), monocarboxylic acids (L-lactate), neutral amino acids (L-leucine), dicarboxylic amino acids (L-glutamate) and certain amines of which choline is the main representative. In each case, the transport is stereospecific, saturable and subject to competitive inhibition. Like the compounds mentioned above that seem unlikely to cross the blood brain barrier yet get across through a specific transporter mediated process, there exists a distinct possibility that these charged zwitterionic O-sulfate conjugates (M6S and its analogs) gain access to the blood brain barrier by way of a similar process. Supportive evidence for such a phenomenon comes from the observed carrier mediated mechanism that helps transport the organic anion harmalol sulfate from the hepatocyte into the blood stream (DeVries et al., 1985).

Receptor Binding

The results of binding studies using guinea pig brain homogenates are presented in Tables 2-1 through 2-6. M6S and M3A6S displayed a greater affinity than that of morphine to mu and kappa$_3$ receptors. Both compounds were even more mu-selective than DAMGO, a mu-preferring peptide. M6S also had greater affinity than that of morphine to delta receptors. Both M6S and M3A6S bound kappa$_1$ sites weakly in guinea pig brain homogenate. In addition M3A6S showed a better ability to discriminate between mu and delta sites than morphine ($K_i$ mu/$K_i$ delta=0.0026 and 0.043 for M3A6S and morphine, respectively) In contrast, the $K_i$ of the non-analgesic compounds M3B6S and MM3A6S were 15× and 14× greater than that of morphine for mu-receptor site and exhibited much greater $K_i$'s for delta, kappa$_3$ and kappa$_1$ sites.

In Vitro Functional Assays (Guinea Pig Ileum and Mouse Vas Deferens)

The effects of opioids standards and the synthetic derivatives of morphine on electrically stimulated contraction of guinea pig ileum (enriched in mu sites) and mouse vas deferens (enriched in delta sites) and their selectivity to opioid receptors are shown in table 4. M6S, M3A6S, and M3B6S all inhibited electrically induced twitches of GPI. M3A6S showed the highest potency followed by M6S >M3B6S. MM3A6S showed no activity on GPI. All four compounds displayed weak activity in MVD assay. Based on their activities in both tissues, M3A6S and M6S exhibited more selective mu activity.

TABLE 2-1

IN VITRO BIOASSAY RESULTS

| Compound SRI # | Guinea Pig Ileum | | | | | | Mouse Vas Deferens | | | |
|---|---|---|---|---|---|---|---|---|---|---|
| | IC$_{50}$ (nM) | DR with CTAP | $K_e$ of CTAP | Ratio | DR with Nor-BNI | $K_e$ of Nor-BNI | Ratio | IC$_{50}$ (nM) | DR with Naltrindole | $K_e$ of Naltrindole | Ratio |

SUBMITTING CHEMIST: PETER CROOKS

| | | | | | | | | | | | |
|---|---|---|---|---|---|---|---|---|---|---|---|
| 20,264 M3A6S | 25.95 ± 5.30 (4) | 5.40 ± 0.18 (2) | 22.73 ± 0.91 (2) | 0.851 | 1.39 ± 0.14 (2) | 54.42 ± 19.6 (2) | 0.001 | a | — | — | — |
| 20,265 DM3A6S | 37.73 ± 6.55 (4) | 6.03 ± 0.97 (2) | 20.25 ± 3.92 (2) | 0.955 | 1.33 ± 0.17 (2) | 68.85 ± 35 (2) | 0.001 | 1,110 ± 451 (3) | 0.924 ± 0.64 (4) | ND | — |
| 20,266 M6S | 66.99 ± 12.14 (4) | 5.00 ± 2.16 (2) | 29.18 ± 15.7 (2) | 0.663 | 0.87 ± 0.06 (2) | N.D. | | b | — | — | — |
| 20,267 DNaM6S | 168.86 ± 32.26 (4) | 6.09 ± 0.53 (2) | 19.75 ± 2.06 (2) | 0.979 | 1.24 ± 0.10 (2) | 90.88 ± 38 (2) | 0.001 | c | — | — | — |
| 20,268 M3S | d | — | — | — | — | — | — | e | — | — | — |
| 20,269 MM3A6S | f | — | — | — | — | — | — | g | — | — | — |
| 20,270 M3Pr6S | 154.42 ± 48.61 (4) | 366 ± 0.15 (2) | 37.58 ± 2.09 (2) | 0.515 | 1.26 ± 0.33 (2) | 40.73 (1) | 0.002 | h | — | — | — |

[a]Very shallow dose-response curve. No IC$_{50}$ could be determined. Maximum inhibition at 2 × 10$^{-4}$ M = 30%.
[b]Very shallow dose-response curve. No IC$_{50}$ could be determined.
[c]Very shallow does-response curve. In 5 of 8 determinations, no IC$_{50}$ value could be determined.
[d,e]No $\mu$, δ, or κ agonist/antagonist activity was found.
[f]No $\mu$/κ agonist/antagonist activity was found.
[g]No IC$_{50}$ could be determined. Maximum inhibition at 2 × 10$^{-4}$ M = 20.0%.
[h]No IC$_{50}$ could be determined. Maximum inhibition at 2 × 10$^{-5}$ M = 20.0%.
Dose Ratio (DR) = IC$_{50}$ in the presence of antagonist/IC$_{50}$ in the absence of antagonist. The number of observations are given in parentheses.

TABLE 2-2

IN VITRO BIOASSAY RESULTS

| Com-pound SRI # | Guinea Pig Ileum | | | | | | | Mouse Vas Deferens | | | |
|---|---|---|---|---|---|---|---|---|---|---|---|
| | IC$_{50}$ (nM) | DR with CTAP | K$_e$ of CTAP | Ratio | DR with Nor-BNI | K$_e$ of Nor-BNI | Ratio | IC$_{50}$ (nM) | DR with Naltrindole | K$_e$ of Naltrindole | Ratio |

SUBMITTING CHEMIST: PETER CROOKS

| Com-pound SRI # | IC$_{50}$ (nM) | DR with CTAP | K$_e$ of CTAP | Ratio | DR with Nor-BNI | K$_e$ of Nor-BNI | Ratio | IC$_{50}$ (nM) | DR with Naltrindole | K$_e$ of Naltrindole | Ratio |
|---|---|---|---|---|---|---|---|---|---|---|---|
| 20,271 M3iBu6S | 1,955 ± 540 (3) | 9.45 ± 4.31 (2) | 13.55 ± 6.89 (2) | 1.427 | 1.38 ± 0.01 (2) | 53.14 ± 1.30 (2) | 0.001 | i | — | — | — |
| 20,272 M3P6S | 69.29 ± 25 (4) | 4.50 ± 0.14 (2) | 28.60 ± 1.15 (2) | 0.676 | 1.13 ± 0.01 (2) | 154.77 ± 16.8 (2) | 0.0004 | j | — | — | — |
| 20,273 M3B6S | 657.50 ± 130 (4) | 3.68 ± 0.27 (2) | 34.92 ± 3.22 (2) | 0.554 | 1.31 ± 0.13 (2) | 70.73 ± 29.13 (2) | 0.001 | k | — | — | — |
| 20,274 MM3B6S | i | — | — | — | — | — | — | l | — | — | — |
| 20,275 DM3B6S | 649.43 ± 131 (4) | 4.03 ± 1.51 (2) | 37.64 ± 18.74 92 | 0.514 | 1.11 ± 0.06 (2) | 229.32 ± 132 (2) | 0.0003 | m | — | — | — |
| 20,276 C6S | 2,090 ± 714$^n$ (3) | 6.34 ± 0.28 (2) | 18.75 ± 1.00 (2) | 1.032 | 1.33 ± 0.07 (2) | 63.35 ± 15.16 (2) | 0.001 | 5,635 ± 746 (2) | — | — | — |
| 20,277 DHC6S | 3,977 ± 770$^n$ (3) | 10.32 ± 1.37 (2) | 10.84 ± 1.59 (2) | 1.784 | 1.33 ± 0.04 (2) | 61.91 ± 6.74 (2) | 0.001 | 38,382 ± 14,488 (2) | — | — | — |

$^i$No IC$_{50}$ could be determined. Maximum inhibition at $10^{-4}$ M = 38%.
$^j$No IC$_{50}$ could be determined. Maximum inhibition at $2 \times 10^{-5}$ M = 26.20 ± 3.62% (n = 4).
$^k$No IC$_{50}$ could be determined. Maximum inhibition at $10^{-4}$ M = 29.4%.
$^l$The compound did not bind to any of the opioid receptors.
$^m$No IC$_{50}$ could be determined. Maximum inhibition at $10^{-5}$ M = 38.20%.
$^n$After CTAP the agonist concentration response curve became very shallow. IC$_{50}$ was estimated only.

TABLE 2-3

RESULTS OF STANDARD COMPOUNDS IN THE FUNCTINOAL ASSAYS

| Compound | Guinea Pigs Ileum | | | | | | |
|---|---|---|---|---|---|---|---|
| | IC$_{50}$ (nM) | DR with CTAP | K$_e$ of CTAP | Ratio | DR with Nor-BNI | K$_e$ of Nor-BNI | Ratio |
| DAMGO | 8.25 ± 2.0 (13) | 4.98 ± 0.3 (4) | 25.31 ± 2.54 (4) | 1.000 | 1.74 ± 0.14 (6) | 27.67 ± 4.52 (6) | 0.002 |
| Morphine | 24.75 ± 2.4 (4) | 4.27 ± 0.18 (2) | 30.67 ± 1.66 (2) | 0.707 | 1.05 ± 0.06 (2) | 222.22 (1) | 0.003 |
| Normorphine | 47.30 ± 13 (15) | 3.02 ± 0.28 (4) | 50.25 ± 6.6 (4) | 0.500 | 1.90 ± 0.39 (4) | 26.47 ± 13.6 (4) | 0.002 |
| Dihydromorphine | 42.39 ± 6.61 (3) | 12.46 ± 0.15 (2) | 17.46 ± 0.23 (2) | 1.354 | 1.12 ± 0.18 (2) | | |
| Fontanyl | 1.86 ± 0.64 (8) | 3.12 ± 0.82 (4) | 53.86 ± 23.10 (4) | 0.403 | 1.18 ± 0.09 (2) | 132.6 ± 69.6 (2) | 0.001 |
| Etonitazone | 0.89 ± 0.15 (4) | 10.38 ± 0.67 (2) | 10.69 ± 0.76 (2) | 2.028 | 1.70 ± 0.27 (2) | 30.64 ± 11.84 (2) | 0.002 |
| A-PL017 | 18.11 ± 2.83 (4) | 7.19 ± 0.74 (2) | 16.29 ± 1.96 (2) | 1.331 | 1.49 ± 0.15 (2) | 43.27 ± 13.2 (2) | 0.001 |
| (−)Methadone | 45.83 ± 3.6 (3) | 1.19 ± 0.14 (4) | 408 ± 100 (3) | 0.062 | 1.20 ± 0.06 (2) | 108.3 ± 35.4 (2) | 0.001 |
| Oxycodone | 323.80 ± 116 (4) | 2.30 ± 0.25 (2) | 78.66 ± 15 (2) | 0.322 | 1.45 ± 0.10 (3) | 45.84 ± 11.5 (3) | 0.001 |
| Nalorphine | 29.20 ± 1.15$^a$ (9) | 0.90 ± 0.14 (2) | N.D. | | 643.9 ± 83.5 (2) | 0.03 ± 0.004 (2) | 2.000 |
| β-Endorphin | 59.43 ± 6.26 (4) | 5.86 ± 0.79 (2) | 20.87 ± 3.37 (2) | 0.928 | 4.24 ± 1.55 (2) | 6.98 ± 3.34 (2) | 0.007 |
| NalBzoH | b | | b | | | | |
| Nalmetene | c | | c | | | | |
| Naloxone | d | | d | | | | |
| Naltrexone | e | | e | | | | |
| CTAP | f | | | | | | |

| Compound | Mouse Vas Deferens | | | |
|---|---|---|---|---|
| | IC$_{50}$ (nM) | DR with Naltrindole | K$_e$ of Naltrindole | Ratio |
| DAMGO | 177.60 ± 134 (7) | 0.93 ± 0.10 (4) | N.D. | |

TABLE 2-3-continued

RESULTS OF STANDARD COMPOUNDS IN THE FUNCTINOAL ASSAYS

| | | | | | |
|---|---|---|---|---|---|
| | | 2,131 ± 904 (4) | 0.92 ± 0.38 (4) | N.D. | |
| | Normorphine | 511.9 ± 51 (4) | 1.06 ± 0.07 (4) | 8.38 ± 0 (2) | 0.0025 |
| | Dihydromorphine | 8.113 ± 2.279 (3) | 2.67 ± 0.82 (2) | | |
| | Fontanyl | 18.07 ± 3.0 (3) | 0.87 ± 0.07 (3) | N.D. | |
| | Etonitrazone | 1.85 ± 0.07 (2) | 0.82 ± 0.11 (2) | N.D. | |
| | A-PL017 | 240.5 ± 63 (2) | 0.89 ± 0.11 (4) | N.D. | |
| | (−)Methadone | 452.5 ± 251 (2) | 0.94 ± 0.09 (2) | N.D. | |
| | Oxycodone | 6,330 ± 3,140 (3) | 0.79 ± 0.08 (2) | N.D. | |
| | Nalorphine | a | | | |
| | β-Endorphin | 67.99 ± 19.0 (3) | 7.98 ± 2.3 (4) | 0.156 ± 0.05 (4) | 0.147 |
| | NalBzoH | b | | | |
| | Nalmetene | c | | | |
| | Naloxone | d | | | |
| | Naltrexone | e | | | |
| | CTAP | | | | |

[a] Nalorphine is a κ-opoid receptor agonist and a μ/δ receptor antagonist. In the GP1 the μ antagonist activity was determined in the presence of 20 nM Nor-BNI. Its $pA_2$ value at the μ is 7.49/−0.87, and at the δ 6.79/−1.05.
[b] NalBzoH is an antagonist at all three opioid receptors. The $pA_2$ value at μ = 6.81/−1.02, at δ = 7.76/−0.96, and at κ = 7.76/−1.19.
[c] Nalmetene is an antagonist at all three opioid receptors. The $pA_2$ value at μ is = 9.38/−1.05, at δ = 7.82/−1.15, and at κ = 8.48/−1.01.
[d] Naloxone is an antagonist at all three opioid receptors. The $pA_2$ value at μ is =6.51/−1.07, at δ = 7.30/−1.05, and at κ = 7.73/−0.99.
[e] Naltrexone is an antagonist at all three opioid receptors. The $pA_2$ value at μ is = 9.19/−1.08, at δ = 1, and at κ = 8.11/−1.03.
[f] CTAP is a very selective μ receptor antagonist. Its $pA_2$ value is 7.65 and the slope = −1.02.

TABLE 2-4

RESULTS OF STANDARD COMPOUNDS IN THE FUNCTINOAL ASSAYS

| | | Guinea Pigs Ileum | | | | | |
|---|---|---|---|---|---|---|---|
| Compound | $IC_{50}$ (nM) | DR with CTAP | $K_e$ of CTAP | Ratio | DR with Nor-BNI | $K_e$ of Nor-BNI | Ratio |
| Buprenorphine | 8.13 ± 3.55[g] (4) | | | | | | |
| DPDPE | 4,130 ± 870 (6) | 5.64 ± 2.6 (3) | 25.83 ± 15.3 (3) | 0.980 (4) | 1.54 ± 0.31 (4) | 50.68 ± 35.1 | 0.001 |
| DSLET | 59.50 ± 3.78 (4) | 5.36 ± 1.35 (4) | 24.50 ± 6.9 (4) | 1.030 | 1.72 ± 0.13 (4) | 28.55 ± 5.6 (4) | 0.002 |
| DTLET | 41.70 ± 14.52 (4) | 5.33 ± 0.04 (2) | 23.12 ± 0.19 (2) | 0.938 | 1.57 ± 0.03 (2) | 35.13 ± 1.74 (2) | 0.002 |
| DADLE | 13.39 ± 7.4 (3) | 4.33 ± 0.60 (2) | 30.58 ± 5.5 (2) | 0.709 | 1.53 ± 0.02 (2) | 38.13 ± 1.54 (2) | 0.002 |
| Leu-Enkephalin* | 87.35 ± 9.90 (4) | 4.63 ± 1.26 (2) | 29.38 ± 10.26 (2) | 0.659 | 1.94 ± 0.04 (2) | 21.41 ± 0.81 (2) | 0.002 |
| Met-Enkephalin* | 27.44 ± 3.75 (4) | 5.08± 0.17 (2) | 24.50 ± 1.06 (2) | 0.791 | 6.07 ± 0.26 (2) | 3.95 ± 0.20 (2) | 0.012 |
| Dynorphin (1.9)* | 4.69 ± 2.34 (4) | 1.13 ± 0.20 (2) | 357.14 (1) | 0.054 | 75.48 ± 26.20 (2) | 0.29 ± 0.10 (2) | 0.161 |
| Naltrindole | h | | h | | | | |
| NTB | i | | i | | | | |
| BNTX | j | | j | | | | |
| TIPPY | | | | | | | |

| | Mouse Vas Deferens | | | |
|---|---|---|---|---|
| Compound | $IC_{50}$ (nM) | DR with Naltrindole | $K_e$ of Naltrindole | Ratio |
| Buprenorphine | 21.39 ± 14.3 (3) | | | |
| DPDPE | 4.11 ± 1.32 (80) | 53.11 ± 17.6 (8) | 0.021 ± 0.007 (8) | 1.000 |

TABLE 2-4-continued

RESULTS OF STANDARD COMPOUNDS IN THE FUNCTINOAL ASSAYS

| | | | | |
|---|---|---|---|---|
| DSLET | 1.23 ± 0.40 (11) | 46.84 ± 8.0 (3) | 0.022 ± 0.004 (3) | 0.955 |
| DTLET | 0.32 ± 0.14 (4) | 31.25 ± 6.7 (4) | 0.034 ± 0.007 (4) | 0.612 |
| DADLE | 1.60 ± 0.30 (4) | 16.22 ± 4.01 (3) | 0.069 ± 0.016 (3) | 0.304 |
| Leu-Enkephalin* | 7.38 ± 2.40 (6) | 28.07 ± 4.45 (6) | 0.038 ± 0.001 (6) | 0.577 |
| Met-Enkephalin* | 1.52 ± 0.26 (3) | 13.63 ± 2.74 (4) | 0.082 ± 0.016 (4) | 0.305 |
| Dynorphin (1.9)* | 12.22 ± 2.59 (4) | 5.71 ± 2.90 (4) | 0.281 ± 0.154 (4) | 0.082 |
| Naltrindole | h | | | |
| NTB | i | | | |
| BNTX | j | | | |
| TIPPY | k | | | |

*Experiments with dynorphins, Met- and Leu-enkephalins were done in the presence of enzyme inhibitors.
[g]The agonist activity could not be reversed neither with CTAP nor with no-BNI. Very high concentration (1.6 × 10$^{-5}$ M) of nor-BNI did reverse the agonist activity.
[h]Naltrindole is an antagonist at all three opioid receptors. The pA$_2$ value at μ is 7.53/−1.13, at δ is 10.92/−0.83, and at κ is 7.61/−0.85.
[i]NTB is an antagonist at all three opioid receptors. The pA$_2$ value at μ is /−1, at δ is 10.55/−1.03, and at κ is 7.22/−1.02.
[j]BNTX is an antagonist at all three opioid receptors. The pA$_2$ value at μ is 8.56/−0.93, at δ 8.90/−1.01, and at κ is 7.43/−0.78.
[k]TIPPY is a very selective, competitive δ opioid receptor antagonist. The pA$_2$ value at δ is 9.17/−0.99.

TABLE 2-5

RESULTS OF STANDARD COMPOUNDS IN THE FUNCTINOAL ASSAYS

| | Guinea Pigs Ileum | | | | | | |
|---|---|---|---|---|---|---|---|
| Compound | IC$_{50}$ (nM) | DR with CTAP | K$_e$ of CTAP | Ratio | DR with Nor-BNI | K$_e$ of Nor-BNI | Ratio |
| U 69,593 | 1.66 ± 0.63 (12) | 0.68 ± 0.11 (4) | N.D. | | 363.0 ± 97.0 (7) (8) | 0.06 ± 0.017 | 1.000 |
| U 50,488H | 1.57 ± 0.50 (6) | 0.52 ± 0.06 (2) | N.D. | | 430.1 ± 85.7 (4) | 0.05 ± 0.01 (4) | 1.250 |
| (−)Bremazocine | 0.067 ± 0.015 (4) | 0.83 ± 0.12 (2) | N.D. | | 226.3 ± 34.3 (2) | 0.09 ± 0.014 (2) | 0.445 |
| Etorphine | 0.055 ± 0.016 (4) | 1.54 ± 0.04 (2) | 185.76 ± 14.6 (2) | 0.104 | 2.34 ± 0.18 (2) | 15.03 ± 2.02 (2) | 0.003 |
| (±)EKC | 0.44 ± 0.14 (8) | 0.60 ± 0.09 (4) | N.D. | | 61.20 ± 6.8 (8) | 0.36 ± 0.11 (8) | 0.170 |
| (−)EKC | 0.15 ± 0.01 (4) | 0.62 ± 0.01 (2) | N.D. | | 35.09 ± 8.47 (2) | 0.61 ± 0.15 (2) | 0.076 |
| Cl-077 | 0.15 ± 0.06 (6) | 0.64 ± 0.10 (2) | N.D. | | 275.90 ± 25.0 (3) (3) | 0.07 ± 0.06 (2) | 0.630 |
| Dynorphin (1-8) | 71.76 ± 45.5 (7) | 0.98 ± 0.17 (2) | N.D. | | 18.44 ± 4.63 (4) | 1.21 ± 0.34 (4) | 0.050 |
| Dynorphin (1-11) | 1.03 ± 0.40 (4) | 0.34 ± 0.02 (2) | N.D. | | 116.49 ± 21.2 (4) | 0.18 35 0.03 (2) | 0.261 |
| Dynorphin (1-13)OH | 0.17 ± 0.07 (4) | 1.05 ± 0.57 (2) | 222.22 (1) | 0.098 | 425.30 40.4 (3) | 0.05 ± 0.01 (4) | 0.979 |
| Dynorphin (1-13)NH$_2$ | 0.38 ± 0.18 (4) | 1.33 ± 0.17 (2) | 349.21 ± 179 (2) | 0.056 | 125.81 ± 14.3 (2) | 0.16 ± 0.02 (2) | 0.286 |
| Dynorphin A (1-17) | 0.95 ± 0.08 (2) | 1.52 ± 0.21 (20 | 209.89 ± 86 (2) | 0.121 | 102.20 ± 11.0 (2) | 0.20 ± 0.02 (2) | 0.302 |
| Dynorphin B | 4.40 ± 1.54 (4) | 1.08 ± 0.30 (2) | 344.83 (1) | 0.056 | 75.48 ± 26.2 (2) | 0.28 ± 0.10 (2) | 0.161 |
| Nor-BNI | m | | | | m | | |

| | Mouse Vas Deferens | | |
|---|---|---|---|
| Compound | IC$_{50}$ (nM) | DR with Naltrindole | K$_e$ of Naltrindole | Ratio |
| U 69,593 | 208.30 ± 1.39 (8) | 0.40 ± 0.10 (4) | N.D. | |
| U 50,488H | 94.33 ± 16.2 (3) | 0.94 ± 0.20 (2) | N.D. | |
| (−)Bremazocine | l | | | |
| Etorphine | 1.39 ± 0.20 (4) | 0.82 ± 0.11 (4) | N.D. | |

TABLE 2-5-continued

RESULTS OF STANDARD COMPOUNDS IN THE FUNCTINOAL ASSAYS

| | (±)EKC | 18.98 ± 7.0 (8) | 0.88 ± 0.09 (4) | N.D. | |
| --- | --- | --- | --- | --- | --- |
| | (−)EKC | 5.31 ± 1.89 (4) | 0.90 ± 0.15 (4) | N.D. | |
| | Cl-977 | 3.71 ± 2.40 (4) | 0.89 ± 0.10 (4) | N.D. | |
| | Dynorphin (1-8) | 56.40 ± 5.0 (3) | 2.77 ± 0.68 (3) | 0.64 ± 0.29 (3) | 0.033 |
| | Dynorphin (1-11) | 368.92 ± 56.0 (4) | 0.75 ± 0.12 (4) | N.D. | |
| | Dynorphin (1-13)OH | 5.28 ± 2.2 (4) | 0.89 ± 0.33 (4) | N.D. | |
| | Dynorphin (1-13)NH$_2$ | 7.02 ± 2.44 (4) | 0.99 ± 0.09 (4) | N.D. | |
| | Dynorphin A (1-17) | 29.30 ± 24.9 (2) | 1.15 ± 0.05 (2) | 7.32 ± 2.5 (2) | 0.003 |
| | Dynorphin B | 39.14 ± 7.39 (4) | 2.10 ± 0.30 (4) | 0.95 ± 0.21 (4) | 0.024 |
| | Nor-BNI | $^m$ | | | |

*Experiments with dynorphines were done in the presence of enzyme inhibitors.
$^l$IC$_{50}$ could not be determined. Very shallow close-response curve.
$^m$Nor-BNI is a selective κ antagonist. Its pA$_2$ value at the κ receptor is 10.02 and the slope is −1.14. The pA$_2$ value at the μ receptor is 7.26/−1.19 and at the δ receptor 7.67/−1.04

TABLE 2-6

RESULTS OF STANDARD COMPOUNDS IN THE FUNCTIONAL ASSAYS

| | | Guinea Pig Ileum | | | | | | Mouse Vas Deferens | | |
| --- | --- | --- | --- | --- | --- | --- | --- | --- | --- | --- |
| Compound | IC$_{50}$ (nM) | DR with CTAP | K$_e$ of CTAP | Ratio | DR with Nor-BNI | K$_e$ of Nor-BNI | Ratio | IC$_{50}$ (nM) | DR with Naltrindole | K$_e$ of Naltrindole | Ratio |
| (−)SKF 10.047 | 10.50 ± 3.9$^n$ (7) | 0.44 ± 0.02 (2) | N.D. | | 273.10 ± 47 (2) | 0.08 ± 0.01 (2) | 0.800 | $^n$ | | |
| (−)Pentazocine | 170.30 ± 69.2 (4) | 0.73 ± 0.38 (2) | N.D. | | 6.10 ± 1.00 (2) | 4.00 ± 0.8 (2) | 0.015 | $^o$ | | |
| (−)Cyclezocine | 1.05 ± 0.4 (4) | 1.00 ± 0.00 (2) | N.D. | | 33.39 ± 25.2 (2) | 0.89 ± 0.69 (2) | 0.067 | $^p$ | | |

$^n$In the GPI the μ antagonist activity was determined in the presence of 20 nM Nor-BNI. The pA$_2$ value is 7.69/−1.22. In the MVD from $10^{-9}$ to $10^{-6}$ M slight inhibition from $5 \times 10^{-6}$ to $5 \times 10^{-5}$ enhancement
$^o$IC$_{50}$ could not be determined. Control (HCl + H$_2$O) caused 50% inhibition
$^p$IC$_{50}$ could not be deterined from $10^{-9}$ to $5 \times 10^{-5}$ M (maximum inhibition 17%)

The data from this study clearly show that esterification of the 3-hydroxyl group of M6S with an acetyl group affords a morphine derivative that has enhanced duration of action as M6S when administered via the sc route in the rat. Both M6S and M3A6S have a more prolonged duration of action than an equimolar dose of morphine given sc (FIG. 2). More importantly, when given icv, M3A6S enhanced duration of action than M6S as an analgesic see FIG. 3), and both M6S and M3A6S possessed greater activity than morphine via this route. Interestingly, the 3-O-benzoyl ester of M6S exhibited extremely weak antinociceptive activity via the sc route, and was essentially devoid of activity when administered icv at doses equimolar to morphine used in this study. We attribute this result to metabolic factors, and propose that the activities of the two esters are related to their susceptibilities to in vivo enzymatic cleavage by esterases to M6S. Thus, the acetyl group in M3A6S would be expected to be rapidly cleaved in vivo, whereas the corresponding benzoate ester would be relatively resistant to esterolysis. Therefore, one may regard M3A6S as a prodrug form of M6S. However, both compounds M6S and M3A6S showed high affinity binding to mu opioid receptors in our in vitro binding assay using guinea pig brain homogenate.

The observation that both M6S and M3A6S are active with a rapid onset of antinociception after icv and sc administration, strongly suggests that these morphine derivatives, like the 6-O-glucuronide conjugates, are capable of penetrating the blood-brain barrier after peripheral administration, in spite of their zwitterionic nature at physiological pH. However, further studies are necessary to determine if the analgesic properties of M6S and M3A6S are due to subsequent cleavage of the sulfate moiety, by sulfatases present in either the periphery or the central nervous system, to form morphine.

Addition of a sulfate group to the 6 position of morphine, as in M6S and M3A6S seems to favor mu- and kappa-like activity, since such alteration displayed more selectivity For mu- receptors (3-fold greater than morphine) and kappa$_3$ receptors (2.2-fold greater than morphine) in our receptor binding assay. Furthermore, M3A6S showed better ability to discriminate between mu- and delta-sites than did morphine or even DAMGO, a mu- preferring peptide, in receptor binding assay using guinea pig brain homogenate. This selectivity has also been supported by its high potency in GPI (enriched in mu-sites) and decreased potency in the MVD (enriched in delta-sites) preparations.

Increasing the polarity of the M3A6S molecule by quaternization of the tertiary amino group to form N-methylmorphinium-6-O-sulfate betaine (MM3A6S) abolished all antinocicentive activity following peripheral or central administration at doses equimolar to morphine used in this study. It seems that this dipolar derivative is unable to interact with CNS opioid receptors because it is inactive via the icv route. In addition, it lacks activity in both GPI and MVD assays and shows weak binding affinity to opioid receptors in our receptor binding assay using guinea pig brain homogenate. These results indicate that a protonated tertiary amino group is a structural requirement for antinociceptive activity in morphine-6-O-sulfate derivatives.

These results indicate that lipophilicity alone is not a determinant of analgesic activity in these novel morphine derivatives. These modified effects of morphine by the conjugations at the 3- and 6-position, appear to be due to their altered interactions with opioid receptors The in vitro bioassay results for opiate receptor binding and functional activity testing were provided by National Institute on Drug Abuse (NIDA), Medication Development Division Contract no. 271-89-8159 awarded to SRI International (Menlo Park, Calif.).

DETAILED DESCRIPTION OF THE FIGS. 1–3

FIG. 1. Structures of morphine and morphine-6-O-sulfate derivatives.

FIG. 2. Antinociceptive response to subcutaneous treatment with morphine. Antinociception is shown as the percent of maximum possible response in the tail-flick test. Free base morphine was used for subcutaneous administration (5 mg/kg, 0.0175 mmole). Equimolar doses of morphine derivatives were as follows: M6S (6.4 mg/kg); M3A6S (7.1 mg/kg); M3B6S (8.2 mg/kg); and MM3A6S (7.4 mg/kg) were administered subcutaneously. Predrug response latencies for saline, morphine, M6S, M3A6S, M3B6S, and MM3A6S were 2.15, 1.96, 2.37, 1.79, 1.95 and 2.11 seconds respectively. Analysis of variance revealed a highly significant treatment by time interaction. Represents a significant difference ($p<0.005$) of morphine, M6S and M3A6S from the corresponding response to saline, M3B6S and MM3A6S treated rats. ¥ Represents a significant difference ($p<0.0006$) of M6S and M3A6S from the corresponding response to saline, M3B6S and MM3A6S treated rats. Represents a significant difference ($p<0.0001$) of M6S and M3A6S from the corresponding response to morphine and M3B6S treated rats. Represents a significant difference ($p<0.0007$) of M6S and M3A6S from the corresponding response to morphine. – Represents a significant difference ($p<0.0007$) of M3A6S from the corresponding response to M3B6S treated rats. ¶ Represents a significant difference ($p<0.004$) of morphine, M6S and M3A6S from the corresponding response to morphine treated rats. Comparisons were made using two-way repeated measure ANOVA followed by Tukey's test. Numbers in parentheses represent the number of rats per group.

FIG. 3. Antinociceptive response to treatment with saline vehicle, morphine and morphine derivatives. For intracerebroventricular drug administration, 2 doses of morphine were used; low dose morphine (0.236 µg/rat, 0.83 pmole µmole/rat as free base) and high dose of morphine (23.6 µg/rat, 83 pmole/rat). Doses of morphine derivatives administered intracerebroventricularly were equimolar to the low dose of morphine and were as follows: M6S (0.22 µg/kg) ; M3A6S (0.25 µg/kg) ; M3B6S (0.29 µg/kg); and MM3A6S (0.26 µg/kg). Antinociception is shown as the percent of maximum possible response in the tail-flick test. Predrug response latencies for saline, morphine low dose, morphine high dose, M6S, M3A6S, M3B6S, and MM3A6S were 2.05, 2.06, 1.69, 1.92, 2.62, 2.06 and 1.82 seconds respectively. Analysis of variance revealed a highly significant treatment by time interaction. Represents a significant difference ($p<0.009$) of M6S from the corresponding response to saline, M3B6S and MM3A6S treated rats. ¶ Represents a significant difference ($p<0.0001$) of M6S and M3A6S from the corresponding response to morphine high dose, saline, M3B6S, MM3A6S and morphine low dose treated rats. * Represents a significant difference ($p<0.0001$) of morphine high dose, M6S and M3A6S from the corresponding response to MM3A6S, morphine low dose, M3B6S and saline treated rats. § Represents a significant difference ($p<0.0001$) of morphine high dose and M3A6S from the corresponding response to M3B6S, saline, MM3A6S and morphine low dose. ¥ Represents a significant difference ($p<0.001$) of morphine high dose from the corresponding response to M3B6S, MM3A6S, saline, M6S and morphine low dose treated rats. – Represents a significant difference ($p<0.004$) of morphine I from the corresponding response to MM3A6S, M3B6S, M3A6S, M6S and saline treated rats. Comparisons were made using two-way repeated measure ANOVA followed by Tukey's test. Numbers in parentheses represent the number of rats per group.

PHARMACEUTICAL PREPARATION AND ADMINISTRATION

The compounds of the invention can be employed as the free amino sulfonic acid zwitterion, or in a salt form (i.e. sodium, potassium, calcium salts for example)

The administration of the compounds may be by inhalation (i.e. an aerosol or nasal formulation); topically in the form of an ointment, cream or lotion; orally, e.f. either as a solid dosage form (i.e. within a solid carrier such as a tablet, hard gelatin capsule or time release capsule); or as a liquid formulation, (i.e. dissolved in a solution or as a suspension, emulsion, or mixture of liquids); transdermally by a transdermal patch.

The pharmacologically effective dosage of the compounds will require their administration in an amount less than $1\times10^{-3}$ mg/kg body weight/day. Most often, the compounds are administered in an amount from $1\times10^{-5}$ but less than $1\times10^{-3}$ mg/kg body weight/day, frequently between $1\times10^{-4}$ but less than $1\times10^{-3}$ mg/kg body weight/day, and preferably between $1\times10^{-4}$ but less than $1\times10^{-5}$ mg/kg body weight/day.

REFERENCES

1. Abbott, F. V.; Palmour, R. M. Morphine-6-glucuronide: analgesic effects and receptor binding profile in rats. Life Sci. 43: 1685–1695; 1988.
2. Brown, E. C.; Roerig, S. C.; Burger, V. T.; Cody, R. B.; Fujimoto, J. M. Analgesic potencies of morphine 3- and 6-sulfates after intracerebroventricular administration in mice: relationship of structural characteristics defined by mass spectrometry and nuclear magnetic resonance. J. Pharm. Sci. 74: 821–824; 1985.
3. Christensen, C. B.; Jorgensen, L. N. Morphine-6-glucuronide has high affinity for the opioid receptor. Pharmacol. Toxicol. 60: 75–76; 1987.
4. D'Amour, F. E.; Smith, D. L. A method for determining loss of pain sensation. J. Pharmacol. Exp. Ther. 72: 74–79; 1947.
5. Davenport, K. E.; Houdi, A. A.; Van Loon, G. R. Nicotine protects against µ-opioid receptor antagonism by β-funaltrexamine: evidence for nicotine-induced release of endogenous opioids in brain. Neurosci. Lett. 113: 40–46; 1990.
6. Hughes, J.; Kosterlitz, H. W.; Leslie, F. M. Assessment of the agonist and antagonist activities of narcotic analgesic drugs by means of the mouse vas deferens. Br. J. Pharmacol. 51: 139p–140p; 1974.
7. Kramer, T. H.; Shook, J. E.; Kazmierski, W.; Ayres, E. A.; Wire, W. S.; Hruby, V. J.; Burks, T. F. Novel peptidic Mu opioid antagonists: Pharmacologic characterization in vitro and in vivo. J. Pharmacol. Exp. Ther. 249: 544–551; 1989.

8. Mori M.-A.; Oguri K.; Yoshimura H.; Shimomura K.; Kamata O.; Ueki S. Chemical Synthesis and analgesic effect of morphine ethereal sulfates. Life Sci. 11: 525–533; 1972.
9. Mulder, G. J. Pharmacological effects of drug conjugates: is morphine-6-glucuronide an exception. Trends Pharmacol. Sci. 13: 302–304; 1992.
10. Oguri, K.; Yamada, M. I.; Shigezane, J.; HIrano, T.; Yoshimura, H. Enhanced binding of morphine and nalorphine to opioid delta receptor by glucuronate and sulfate conjugations at the 6-position. Life Sci. 41: 1457–1464; 1987.
11. Osborne, R. J.; Joel, S. P.; Trew, D.; Slevin, M. L. Analgesic activity of morphine-6-glucuronide. Lancet I: 828; 1988.
12. Osborne, R.; Joel, S.; Trew, D.; Slevin, M. Morphine and metabolite behavior after different routes of morphine administration: determination of the importance of the active metabolite morphine-6-glucuronide. Clin. Pharmacol. Ther. 47: 12–19; 1990.
13. Paton, W. D. M.; Vizi, E. S. The inhibitory action of noradrenaline and adrenaline on acetylcholine output by guinea-pig ileum longitudinal muscle strip. Br. J. Pharmacol. 35: 10–28; 1969.
14. Paul, D.; Standifer, K. M.; Inturrisi, C. E; Pasternak, G. W. Pharmacological characterization of morphine-6β-glucuronide, a very potent morphine metabolite. J. Pharmacol. Exp. Ther. 251: 477–483; 1989.
15. Portoghese, P S.; Lipkwski, A W.; Takemori, A. E. Binaltorphimine and nor-binaltorphimine, potent and selective κ-opioid receptor antagonists. Life Sciences 40: 1287–1292; 1987.
16. Portoghese, P S.; Sultana, M.; Takemori, A. E. Naltrindole, a highly selective and potent non-peptide δ_opioid receptor antagonist. Eur. J. Pharmacol. 146: 185–186; 1988.
17. Ronai, A. Z.; Graf, L.; Szekely, J. I.; Dunai-Kovacs, Z.; Bajusz, S. Differential behavior of LPH-(61–91)-peptide in different model systems comparison of the opioid activities of LPH-(61–91)-peptide and its fragments. FEBS Lett. 74:182–184;197.
18. Sawe, J.; Kager, L.; Svensson, J. O.; Rane, A. Oral morphine in cancer patients: in vivo kinetics and in vitro hepatic glucuronidation. Br. J. clin. Pharmacol. 19: 495–501; 1985.
19. Sear, J. W.; Hand, C. W.; Moore, R. A.; McQuay, H. J. Studies on morphine disposition: influence of renal failure on the kinetics of morphine and its metabolites. Brit. J. Anesthesia 62: 28–32; 1989.
20. Yoshimura, H. Ida, S.; Oguri, K.; Tsukamoto, H. Biochemical basis for analgesic activity of morphine-6-glucuronide-I: Penetration of morphine-6-glucuronide in the brain of rats. Biochem. Pharmacol. 22: 1423–1430; 1973.

The purpose of the above description and examples is to illustrate some embodiments of the present invention without implying any limitation. It will be apparent to those of skill in the art that various modifications and variations may be made to the composition and method of the present invention without departing from the spirit or scope of the invention. All patents and publications cited herein are incorporated by reference in their entireties.

We claim:

1. A method of treating pain comprising administering to a person in need thereof a therapeutically effective amount of a compound selected from the group consisting of the following formulas I and II:

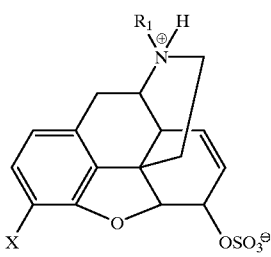

Formula I wherein X is selected from the group consisting of —OR2,

and

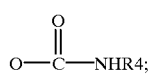

wherein $R_1$ may be a straight or branched chain alkyl group having 1–5 carbon atoms or alkenyl group having 2–5 carbon atoms,
wherein R2 is an alkyl having 1–3 carbon atoms,
wherein R3 is H, n-alkyl, or branched alkyl with 2–10 carbon atoms, cycloalkyl with 3–10 carbon atoms, aralkyl with 5–10 carbon atoms, phenyl, n-alkenyl or branched alkenyl with 2–10 carbon atoms, and n-alkynyl or branched alkynyl with 2–10 carbon atoms, and
wherein R4 is H or n-alkyl or branched alkyl with 1–10 carbon atoms, cycloalkyl with 3–10 carbon atoms, aralkyl with 5–10 carbon atoms, n-alkenyl or branched alkenyl with 2–10 carbon atoms, and n-alkynyl or branched alkynyl with 2–10 carbon atoms, with the proviso that when R3 is a methyl group, $R_1$ is neither a methyl group nor —CH$_2$—CH=C(CH$_3$)$_2$ group; and

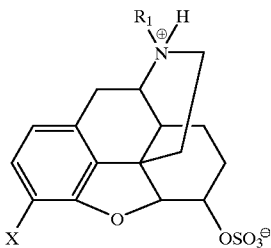

Formula II wherein X is selected from the group consisting of —OR2,

and

wherein $R_1$ may be straight or branched chain alkyl group having 1–5 carbon atoms or alkenyl group having 2–5 carbon atoms, wherein R2 is an alkyl having 1–3 carbon atoms, wherein R3' is H, n-alkyl, or branched alkyl with 2–10 carbon atoms, cycloalkyl with 3–10 carbon atoms, aralkyl with 5–10 carbon atoms, n-alkenyl or branched alkenyl with 2–10 carbon atoms, and n-alkynyl or branched alkynyl with 2–10 carbon atoms, and wherein R4 is H or n-alkyl or branched alkyl with 1–10 carbon atoms, cycloalkyl with 3–10 carbon atoms, aralkyl with 5–10 carbon atoms, n-alkenyl or branched alkenyl with 2–10 carbon atoms, and n-alkynyl or branched alkynyl with 2–10 carbon atoms, with the proviso that when R3 is a methyl group, $R_1$ is not a methyl group.

2. A method according to claim 1, formula I, wherein R3 is n-alkyl or branched alkyl with 4–8 carbon atoms.

3. A method according to claim 1, formula I wherein X is selected from the group consisting of $OCH_3$, $OCOCH_3$, $OCOCH_2CH_3$, $OCOCH(CH_3)_2$, $OCOC(CH_3)_3$ and OCO-phenyl.

4. A method according to claim 1, formula I wherein X is $OCOCH_2CH_3$.

5. A method according to claim 1, formula I wherein X is $OCOCH(CH_3)_2$.

6. A method according to claim 1, formula I wherein X is $OCOC(CH_3)_3$.

7. A method according to claim 1, formula I wherein X is OCO-phenyl.

8. A method according to claim 1, formula II wherein X is $OCH_3$.

9. A method according to claim 1, formula II wherein X is $OCOCH_3$.

10. A method according to claim 1, formula II wherein X is selected from the group consisting of $OCH_3$, $OCOCH_3$ and $OCOCH_2CH_3$.

* * * * *